(12) United States Patent
De Beuckeleer et al.

(10) Patent No.: US 7,928,295 B2
(45) Date of Patent: Apr. 19, 2011

(54) HERBICIDE TOLERANT RICE PLANTS AND METHODS FOR IDENTIFYING SAME

(75) Inventors: Marc De Beuckeleer, Zwijnaarde (BE); Kirk Johnson, Davis, CA (US); Frank Michiels, Bangkok (TH)

(73) Assignee: Bayer Bioscience N.V., Ghent (BE)

( * ) Notice: Subject to any disclaimer, the term of this patent is extended or adjusted under 35 U.S.C. 154(b) by 718 days.

(21) Appl. No.: 11/844,847

(22) Filed: Aug. 24, 2007

(65) Prior Publication Data

US 2008/0289060 A1     Nov. 20, 2008

Related U.S. Application Data

(60) Provisional application No. 60/839,736, filed on Aug. 24, 2006.

(51) Int. Cl.
  *A01H 1/00*  (2006.01)
  *C12N 15/82*  (2006.01)
(52) U.S. Cl. ........................... 800/300; 800/266
(58) Field of Classification Search .................. None
  See application file for complete search history.

(56) References Cited

U.S. PATENT DOCUMENTS

| | | |
|---|---|---|
| 5,561,236 A | 10/1996 | Leemans et al. |
| 5,641,664 A | 6/1997 | D'Halluin et al. |
| 5,646,024 A | 7/1997 | Leemans et al. |
| 5,648,477 A | 7/1997 | Leemans et al. |
| 5,679,558 A | 10/1997 | Gobel et al. |
| 5,712,135 A | 1/1998 | D'Halluin et al. |
| 5,739,082 A | 4/1998 | Donn |
| 6,002,070 A | 12/1999 | D'Halluin et al. |
| 6,074,877 A | 6/2000 | D'Halluin et al. |
| 6,333,449 B1 | 12/2001 | Michiels et al. |
| 6,468,747 B1 | 10/2002 | De Beuckeleer et al. |
| 6,933,111 B1 | 8/2005 | De Beuckeleer et al. |

FOREIGN PATENT DOCUMENTS

WO   WO 00/26356   *   5/2000

OTHER PUBLICATIONS

De Block, et al. (1987) *EMBO J.* 6 : 2513-2518.
Hill, et al. (1994) *Aust. J. Exp. Agric.* 34 : 1021-1029.
Thompson, et al. (1987) *EMBO J.* 6 : 2519-2523.

* cited by examiner

*Primary Examiner* — David H Kruse
(74) *Attorney, Agent, or Firm* — Hunton & Williams LLP

(57) ABSTRACT

The invention provides specific transgenic rice plants, plant material and seeds, characterized in that these products harbor a specific transformation event at a specific location in the rice genome. Tools are also provided which allow rapid and unequivocal identification of the event in biological samples.

10 Claims, 2 Drawing Sheets

SEQUENCE LISTING

<160> NUMBER OF SEQ ID NOS: 25

<210> SEQ ID NO 1
<211> LENGTH: 743
<212> TYPE: DNA
<213> ORGANISM: Artificial Sequence
<220> FEATURE:
<223> OTHER INFORMATION: Nucleotide sequence comprising the 5' flanking
      sequence of GAT-OS3
<220> FEATURE:
<221> NAME/KEY: plant DNA
<222> LOCATION: (1)..(603)
<220> FEATURE:
<221> NAME/KEY: misc_feature
<222> LOCATION: (407)..(407)
<223> OTHER INFORMATION: n is a, c, g, or t
<220> FEATURE:
<221> NAME/KEY: insert DNA
<222> LOCATION: (604)..(743)

<400> SEQUENCE: 1
cacatcctca tcctaccatt agtcataagg gaaaaataaa cctttcaccc atagacttat    60
ccatccaaac attagtgtag tccgaagtaa acatagcaat agctaaaaaa aatattgcta   120
tgtttctcta taaatcaagt taaatttaaa gaaatttaag taaattaaaa aaatcaaatc   180
atcttataat ataaaacttg ttataaaact gatggagtac ttgcttggat gagcgtttaa   240
atagataatc gtaacgaaaa gtttaaatag gtatttatac cctatatacc tcataaaact   300
tatcacacat tttgtgtatg ggtatcatca accaacaaat agatagccaa atcacaatca   360
tccaatgcca agcaaggaaa ccaaatcccc caaccaatac aatcacncca aattgccggc   420
ccctatttaa aagtggagcc ccggacaatg gaggatggat atttgctact agtacccgct   480
gactgcagtt gcccttctgg cgagggaaaa tagccggggt gaggttagtg gaaaaacgtt   540
ggtggcccct tttcccctgg ggataaagca cacagctgcc ggtgggcccc accgccgcat   600
gctccagtac tcggccgtcg accgcggtac cccggaattc caatcccaca aaaatctgag   660
cttaacagca cagttgctcc tctcagagca gaatcgggta ttcaacaccc tcatatcaac   720
tactacgttg tgtataacgg tcc                                           743

<210> SEQ ID NO 2
<211> LENGTH: 607
<212> TYPE: DNA
<213> ORGANISM: Artificial Sequence
<220> FEATURE:
<223> OTHER INFORMATION: nucleotide sequence comprising the 3' flanking
      sequence of GAT-OS3
<220> FEATURE:
<221> NAME/KEY: insert DNA
<222> LOCATION: (1)..(72)
<220> FEATURE:
<221> NAME/KEY: plant DNA
<222> LOCATION: (73)..(607)

<400> SEQUENCE: 2
taccgccccg tccggtcctg cccgtcaccg agatctgaga tcacgcgttc taggatccga    60
agcagatcgt tccacctccc aacaataaaa gcgcctgcac actccgcgcc ctcccattgg   120
tccagacaca ccatcgctgg taagtactac tagtactcct acctttttacc cccctcgact   180 ccgaccacac gaagccgatc accctaaccc acttacacgt ggccccgaga tgacttccgg   240
acccacctgt cagtcacatg ggtacgccat cgcgtgtcgt cgaagcgagg cgggatgcgg   300
aggacacgtc gactctgcgc acccgctttt gctggcgggt agggtaggtc aggtgtgggc   360

```
catgggtgtc agtgagggg gagtatttgc tgcttgcccg ctttgcgtgg cacggcaggc    420
aaggcgctcc tcccctctcc aatgggcaat gggccggcgc gggtgcgggc cttttacgtg    480
ccgcgcgcca cgtgttgcgg cgagaccaat catagcccgc tcctccagtg acacgtgggc    540
ctcacgacac gcgtccgttc ccacctccct actcctagct cctagcttgc tccgctgtgt    600
attaaag                                                              607
```

```
<210> SEQ ID NO 3
<211> LENGTH: 21
<212> TYPE: DNA
<213> ORGANISM: Artificial Sequence
<220> FEATURE:
<223> OTHER INFORMATION: Oligonucleotide primer OSA010

<400> SEQUENCE: 3
ctactagtac ccgctgactg c                                              21

<210> SEQ ID NO 4
<211> LENGTH: 21
<212> TYPE: DNA
<213> ORGANISM: Artificial Sequence
<220> FEATURE:
<223> OTHER INFORMATION: Oligonucleotide primer OSA009

<400> SEQUENCE: 4
ggaccgttat acacaacgta g                                              21

<210> SEQ ID NO 5
<211> LENGTH: 22
<212> TYPE: DNA
<213> ORGANISM: Artificial Sequence
<220> FEATURE:
<223> OTHER INFORMATION: Oligonucleotide primer SHA040

<400> SEQUENCE: 5
tctaggatcc gaagcagatc gt                                             22

<210> SEQ ID NO 6
<211> LENGTH: 16
<212> TYPE: DNA
<213> ORGANISM: Artificial Sequence
<220> FEATURE:
<223> OTHER INFORMATION: Oligonucleotide primer SHA041

<400> SEQUENCE: 6
ggagggcgcg gagtgt                                                    16

<210> SEQ ID NO 7
<211> LENGTH: 21
<212> TYPE: DNA
<213> ORGANISM: Artificial Sequence
<220> FEATURE:
<223> OTHER INFORMATION: Oligonucleotide primer YTP172

<400> SEQUENCE: 7
agtagtactt accagcgatg g                                              21

<210> SEQ ID NO 8
<211> LENGTH: 21
<212> TYPE: DNA
<213> ORGANISM: Artificial Sequence
<220> FEATURE:
<223> OTHER INFORMATION: Oligonucleotide primer OSA001
```

```
<400> SEQUENCE: 8
gatcagtgca ggcaatactg g                                              21

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide primer OSA002

<400> SEQUENCE: 9
ttcctaacat gtgggtgtcg                                                20

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide primer KVM159

<400> SEQUENCE: 10
tggtgagcgt tttgcagtct                                                20

<210> SEQ ID NO 11
<211> LENGTH: 22
<212> TYPE: DNA
<213> ORGANISM: Artificial Sequence
<220> FEATURE:
<223> OTHER INFORMATION: Oligonucleotide primer KVM160

<400> SEQUENCE: 11
ctgatccact agcaggaggt cc                                             22

<210> SEQ ID NO 12
<211> LENGTH: 20
<212> TYPE: DNA
<213> ORGANISM: Artificial Sequence
<220> FEATURE:
<223> OTHER INFORMATION: BamHI linker

<400> SEQUENCE: 12
ctgaggtcga ctatcgagtt                                                20

<210> SEQ ID NO 13
<211> LENGTH: 24
<212> TYPE: DNA
<213> ORGANISM: Artificial Sequence
<220> FEATURE:
<223> OTHER INFORMATION: BamHI linker

<400> SEQUENCE: 13
gatcaactcg atagtcgacc tcag                                           24

<210> SEQ ID NO 14
<211> LENGTH: 15
<212> TYPE: DNA
<213> ORGANISM: Artificial Sequence
<220> FEATURE:
<223> OTHER INFORMATION: Oligonucleotide primer YTP110

<400> SEQUENCE: 14
gtcgactatc gagtt                                                     15
```

```
<210> SEQ ID NO 15
<211> LENGTH: 15
<212> TYPE: DNA
<213> ORGANISM: Artificial Sequence
<220> FEATURE:
<223> OTHER INFORMATION: Oligonucleotide primer YTP122

<400> SEQUENCE: 15
actatcgagt tgatc                                                    15

<210> SEQ ID NO 16
<211> LENGTH: 22
<212> TYPE: DNA
<213> ORGANISM: Artificial Sequence
<220> FEATURE:
<223> OTHER INFORMATION: Oligonucleotide primer MLD015

<400> SEQUENCE: 16
tggttcctag cgtgagccag tg                                            22

<210> SEQ ID NO 17
<211> LENGTH: 21
<212> TYPE: DNA
<213> ORGANISM: Artificial Sequence
<220> FEATURE:
<223> OTHER INFORMATION: Oligonucleotide primer MLD016

<400> SEQUENCE: 17
agctgctgct cttgcctctg t                                             21

<210> SEQ ID NO 18
<211> LENGTH: 24
<212> TYPE: DNA
<213> ORGANISM: Artificial Sequence
<220> FEATURE:
<223> OTHER INFORMATION: Oligonucleotide primer MDB010

<400> SEQUENCE: 18
gcaccatcgt caaccactac atcg                                          24

<210> SEQ ID NO 19
<211> LENGTH: 22
<212> TYPE: DNA
<213> ORGANISM: Artificial Sequence
<220> FEATURE:
<223> OTHER INFORMATION: Oligonucleotide primer MDB053

<400> SEQUENCE: 19
catgacgtgg gtttctggca gc                                            22

<210> SEQ ID NO 20
<211> LENGTH: 22
<212> TYPE: DNA
<213> ORGANISM: Artificial Sequence
<220> FEATURE:
<223> OTHER INFORMATION: Oligonucleotide primer YTP160

<400> SEQUENCE: 20
gtaatacgac tcactatagg gc                                            22

<210> SEQ ID NO 21
<211> LENGTH: 19
<212> TYPE: DNA
<213> ORGANISM: Artificial Sequence
<220> FEATURE:
<223> OTHER INFORMATION: Oligonucleotide primer YTP161
```

```
<400> SEQUENCE: 21
actatagggc acgcgtggt                                                    19

<210> SEQ ID NO 22
<211> LENGTH: 48
<212> TYPE: DNA
<213> ORGANISM: Artificial Sequence
<220> FEATURE:
<223> OTHER INFORMATION: blunt-end GW adaptor

<400> SEQUENCE: 22
gtaatacgac tcactatagg gcacgcgtgg tcgacggccc gggctggt                    48

<210> SEQ ID NO 23
<211> LENGTH: 234
<212> TYPE: DNA
<213> ORGANISM: Artificial Sequence
<220> FEATURE:
<223> OTHER INFORMATION: Insertion site of GAT-OS3

<400> SEQUENCE: 23
ctactagtac ccgctgactg cagttgccct tctggcgagg gaaaatagcc ggggtgaggt       60
tagtggaaaa acgttggtgg cccctttcc cctggggata aagcacacag ctgccggtgg      120
gccccaccgc cgcatgctcc agacggtcta cgtgttccct cccaacaata aaagcgcctg    180
cacactccgc gccctcccat tggtccagac acaccatcgc tggtaagtac tact           234

<210> SEQ ID NO 24
<211> LENGTH: 26
<212> TYPE: DNA
<213> ORGANISM: Artificial Sequence
<220> FEATURE:
<223> OTHER INFORMATION: GAT-OS3-specific oligonucleotide

<400> SEQUENCE: 24
ccacctccca acaataaaag cgcctg                                            26

<210> SEQ ID NO 25
<211> LENGTH: 23
<212> TYPE: DNA
<213> ORGANISM: Artificial Sequence
<220> FEATURE:
<223> OTHER INFORMATION: phospholipase D gene-specific oligonucleotide

<400> SEQUENCE: 25
tgttgtgctg ccaatgtggc ctg                                               23
```

HERBICIDE TOLERANT RICE PLANTS AND METHODS FOR IDENTIFYING SAME

CROSS-REFERENCE TO RELATED APPLICATIONS

This application claims benefit of U.S. Provisional Patent Application No. 60/839,736, filed Aug. 24, 2006, the disclosure which is hereby incorporated by reference.

BACKGROUND OF THE INVENTION (i) Field of the Invention

This invention relates to transgenic rice plants, plant material and seeds, characterized by harboring a specific transformation event, particularly by the presence of a gene encoding a protein that confers herbicide tolerance, at a specific location in the rice genome. The rice plants of the invention combine the herbicide tolerant phenotype with an agronomic performance, genetic stability and adaptability to different genetic backgrounds equivalent to the non-transformed rice line in the absence of weed pressure. This invention further provides methods and kits for identifying the presence of plant material comprising specifically transformation event GAT-OS3 in biological samples.

(ii) Description of the Related Art

The phenotypic expression of a transgene in a plant is determined both by the structure of the gene itself and by its location in the plant genome. At the same time the presence of the transgene (in a foreign DNA) at different locations in the genome will influence the overall phenotype of the plant in different ways. The agronomically or industrially successful introduction of a commercially interesting trait in a plant by genetic manipulation can be a lengthy procedure dependent on different factors. The actual transformation and regeneration of genetically transformed plants are only the first in a series of selection steps, which include extensive genetic characterization, breeding, and evaluation in field trials, eventually leading to the selection of an elite event.

Rice production is commonly threatened by various weeds. Some of these can be highly competitive and in cases of severe infestation can result in yield loss of such magnitude that it makes the crop economically unattractive. For direct-seeded, mechanized rice cultivation typical of temperate production, both cultural practices (e.g. crop rotation, irrigation management) and herbicides are necessary to control weeds (Hill et al. 1994, Aust. J. Exp. Agric. 34:1021-1029).

The unequivocal identification of an elite event is becoming increasingly important in view of discussions on Novel Food/Feed, segregation of GMO and non-GMO products and the identification of proprietary material. Ideally, such an identification method is both quick and simple, without the need for an extensive laboratory set-up. Furthermore, the method should provide results that allow unequivocal determination of the elite event without expert interpretation, but which hold up under expert scrutiny if necessary. Specific tools for use in the identification of elite event GAT-OS3 in biological samples are described herein.

U.S. Pat. Nos. 6,333,449, 6,468,747 and 6,933,111 describe transgenic rice plants comprising a glufosinate tolerance gene. Such transgenic rice plants are tolerant to the herbicidal compounds phosphinothricin (PPT, also called glufosinate) or bialaphos (see also for example U.S. Pat. Nos. 5,646,024, 5,648,477 and 5,561,236) and salts and optical isomers thereof.

The transgenic rice plants contain a chimeric gene conferring tolerance to glufosinate, comprising the bar gene (Thompson et al, 1987, EMBO J. 6:2519-2523; Deblock et al. 1987, EMBO J. 6:2513-2518) encoding the enzyme phosphinothricin acetyl transferase (PAT), under control of the 35S promoter from Cauliflower Mosaic Virus (Odell et al., 1985, Nature 313:810-812).

The transformation of monocotyledonous plants is described in U.S. Pat. Nos. 5,641,664, 5,712,135, 6,002,070 and 6,074,877. Transformation of rice with the bar gene by electroporation of aggregated suspension cells is described in U.S. Pat. No. 5,679,558.

However, none of the prior art disclosures teach or suggest the present invention.

SUMMARY OF THE INVENTION

The present invention relates to a transgenic rice plant, or seed, cells or tissues thereof, comprising, stably integrated into its genome, an expression cassette which comprises a herbicide tolerance gene comprising the coding sequence of the bar gene, which is herbicide tolerant and, in the absence of weed pressure, has an agronomic performance which is substantially equivalent to the non-transgenic isogenic line. Under weed pressure and the appropriate glufosinate treatment, the plant will have a superior agronomic phenotype compared to the non-transgenic plant.

In the one embodiment of the invention the rice plant, or seed, cells or tissues thereof, comprise elite event GAT-OS3. The genomic DNA of such rice plant, seed, cells or tissues, is characterized by the fact that, when analyzed in a PCR identification protocol as described herein, using two primers directed to the 5' or 3' flanking region of GAT-OS3 and the foreign DNA, respectively, yields a fragment which is specific for GAT-OS3. The primers may be directed against the 5' flanking region within SEQ ID NO: 1 and the foreign DNA respectively such as the primers comprising or consisting of the nucleotide sequence of SEQ ID NO: 3 and SEQ ID NO: 4 respectively, and yield a DNA fragment of between 260 and 300 bp, preferably of about 278 bp.

Reference seed comprising the elite event of the invention has been deposited at the American Type Culture Collection (ATCC) (10801 University Blvd., Manassas, Va. 20110-2209), under ATCC accession number PTA-2600. One embodiment of the invention is the seed comprising elite event GAT-OS3 deposited under ATTC accession number PTA-2600, which will grow into a rice plant tolerant to glufosinate. The seed of ATCC deposit number PTA-2600, which is a seed lot consisting of about 50% non-transgenic kernels and 50% transgenic kernels hemizygous for the GAT-OS3 event, comprising the elite event of the invention, will grow into glufosinate tolerant rice plants. The seed can be sown and the growing plants can be treated with PPT or Liberty™ as described herein to obtain 100% glufosinate tolerant plants, comprising the elite event of the invention. The invention further relates to cells, tissues, progeny, and descendants from a plant comprising the elite event of the invention grown from the seed deposited at the ATCC having accession number PTA-2600. The invention further relates to plants obtainable by propagation of and/or breeding with a rice plant comprising the elite event of the invention grown from the seed deposited at the ATCC having accession number PTA-2600.

The invention further relates to a method for identifying a transgenic plant, or cells or tissues thereof, comprising elite event GAT-OS3 which method is based on identifying the presence of characterizing DNA sequences or amino acids encoded by such DNA sequences in the transgenic plant, cells or tissues. According to a preferred embodiment of the invention, such characterizing DNA sequences are sequences of 15 bp, preferably 20 bp, most preferably 30 bp or more which comprise the insertion site of the event, i.e., both a part foreign DNA and a part of the rice genome (either the 5' or 3' flanking region) contiguous therewith, allowing specific identification of the elite event.

The present invention further relates to methods for identifying and/or quantifying elite event GAT-OS3 in biological samples, which methods are based on primers and/or probes which specifically recognize the 5' and/or 3' flanking sequence of GAT-OS3.

More specifically, the invention relates to a method comprising amplifying a sequence of a nucleic acid present in biological samples, using a polymerase chain reaction with at least two primers, one of which recognizes the 5' or 3' flanking region of GAT-OS3, the other which recognizes a sequence within the foreign DNA of GAT-OS3, preferably to obtain a DNA fragment of between 50 and 500 bp. The primers may recognize a sequence within the 5' flanking region of GAT-OS3 (SEQ ID NO: 1 from position 1 to position 603) or within the 3' flanking region of GAT-OS3 (complement of SEQ ID NO: 2 from position 73 to position 607) and a sequence within the foreign DNA (complement of SEQ ID NO: 1 from position 604 to 743 or SEQ ID NO: 2 from position 1 to position 72), respectively. The primer recognizing the 5' flanking region may comprise the nucleotide sequence of SEQ ID NO: 3 and the primer recognizing a sequence within the foreign DNA may comprise the nucleotide sequence of SEQ ID NO: 4 described herein. The primer recognizing the 3' flanking region may comprise the nucleotide sequence of SEQ ID NO: 6 and the primer recognizing a sequence within the foreign DNA may comprise the nucleotide sequence of SEQ ID NO: 5 described herein. The method may further comprise the use of at least one fluorescent-labeled probe to detect the amplification of the specific DNA fragment. In one embodiment of the invention such fluorescent-labeled probe is capable of hybridizing to the sequence spanned by the specific primers and generating fluorescence signals upon its release at each PCR cycle. The present invention more specifically relates to a method for identifying and/or quantifying elite event GAT-OS3 in biological samples, which method comprises amplifying a sequence of a nucleic acid present in a biological sample, using a polymerase chain reaction with at least two primers comprising the nucleotide sequence of SEQ ID NO: 5 and SEQ ID NO: 6 respectively and at least one fluorescent-labeled probe comprising the nucleotide sequence of SEQ ID NO: 24 described herein.

The present invention more specifically relates to a method for identifying elite event GAT-OS3 in biological samples, which method comprises amplifying a sequence of a nucleic acid present in a biological sample, using a polymerase chain reaction with two primers having the nucleotide sequence of SEQ ID NO: 3 and SEQ ID NO: 4 respectively, to obtain a DNA fragment of about 278 bp, and to a method for identifying elite event GAT-OS3 in biological samples, which method comprises amplifying a sequence of a nucleic acid present in a biological sample, using a polymerase chain reaction with two primers having the nucleotide sequence of SEQ ID NO: 5 and SEQ ID NO: 6 respectively, to obtain a DNA fragment of about 66 bp. The present invention further relates to a method for identifying and/or quantifying elite event GAT-OS3 in biological samples, which method comprises amplifying a sequence of a nucleic acid present in a biological sample, using a polymerase chain reaction with two primers having the nucleotide sequence of SEQ ID NO: 5 and SEQ ID NO: 6 respectively, to obtain a DNA fragment of about 66 bp, and using a fluorescent-labeled probe comprising the nucleotide sequence of SEQ ID NO: 24, to generate a fluorescence signal if the DNA fragment of 66 bp is produced.

The present invention further relates to the specific flanking sequences of GAT-OS3 described herein, which can be used to develop specific identification methods for GAT-OS3 in biological samples. Such specific flanking sequences may also be used as reference control material in identification assays. More particularly, the invention relates to the 5' and/or 3' flanking regions of GAT-OS3 which can be used for the development of specific primers and probes as further described herein. Also suitable as reference material are nucleic acid molecules, preferably of about 20-100 bp, comprising the sequence which can be amplified by primers having the nucleotide sequence of SEQ ID No. 6 and SEQ ID No. 5. The invention further relates to identification methods for the presence of GAT-OS3 in biological samples based on the use of such specific primers or probes. Primers may consist of a nucleotide sequence of 17 to about 200 consecutive nucleotides selected from the nucleotide sequence of SEQ ID NO: 1 from nucleotide 1 to nucleotide 603 or the complement of the nucleotide sequence of SEQ ID NO: 2 from nucleotide 73 to nucleotide 607 combined with primers consisting of a nucleotide sequence of 17 to about 200 consecutive nucleotides selected from the complement of the nucleotide sequence of SEQ ID NO: 1 from nucleotide 604 to nucleotide 743 or the nucleotide sequence of SEQ ID NO: 2 from nucleotide 1 to nucleotide 72. Primers may also comprise these nucleotide sequences located at their extreme 3' end, and further comprise unrelated sequences or sequences derived from the mentioned nucleotide sequences, but comprising mismatches.

The invention further relates to kits for identifying elite event GAT-OS3 in biological samples, said kits comprising at least one primer or probe which specifically recognizes the 5' or 3' flanking region of GAT-OS3 or the specific rearrangement within the foreign DNA sequence in GAT-OS3.

The kit of the invention may comprise, in addition to a primer which specifically recognizes the 5' or 3' flanking region of GAT-OS3, a second primer which specifically recognizes a sequence within the foreign DNA of GAT-OS3, for use in a PCR identification protocol. The kits of the invention may comprise at least two specific primers, one of which recognizes a sequence within the 5' flanking region of GAT-OS3, and the other of which recognizes a sequence within the foreign DNA, or one of which recognizes a sequence within the 3' flanking region of GAT-OS3, and the other of which recognizes a sequence within the foreign DNA. The primer recognizing the 5' flanking region may comprise the nucleotide sequence of SEQ ID NO: 3 and the primer recognizing the foreign DNA may comprise the nucleotide sequence of SEQ ID NO: 4 or any other primer as described herein. The primer recognizing the 3' flanking region may comprise the nucleotide sequence of SEQ ID NO: 6 and the primer recognizing the foreign DNA may comprises the nucleotide sequence of SEQ ID NO: 5 or any other primer as described herein.

The invention further relates to a kit for identifying elite event GAT-OS3 in biological samples, said kit comprising the PCR primers having the nucleotide sequence of SEQ ID NO: 3 and SEQ ID NO: 4 for use in the GAT-OS3 PCR identification protocol described herein.

The invention also relates to a kit for identifying elite event GAT-OS3 in biological samples, which kit comprises a specific probe comprising a nucleotide sequence which corresponds (or is complementary) to a sequence having between 80% and 100% sequence identity with a specific region of GAT-OS3. Preferably the sequence comprised in the probe corresponds to a specific region comprising part of the 5' or 3' flanking region of GAT-OS3. Most preferably, the specific probe comprises a nucleotide sequence which corresponds (or is complementary) to a sequence having between 80% and 100% sequence identity to the sequence between nucleotide 583 to 624 of SEQ ID NO: 1 or SEQ ID NO: 2 from nucleotide 52 to 93.

The invention further relates to a kit for identifying and/or quantifying elite event GAT-OS3 in biological samples, said kit comprising at least two specific primers, one of which recognizes a sequence within the 5' flanking region of GAT-OS3, and the other of which recognizes a sequence within the foreign DNA, or one of which recognizes a sequence within the 3' flanking region of GAT-OS3, and the other of which recognizes a sequence within the foreign DNA, and at least one specific probe comprising a nucleotide sequence which corresponds (or is complementary) to a sequence having between 80% and 100% sequence identity with a specific region of GAT-OS3. The present invention more specifically relates to a kit for identifying and/or quantifying elite event GAT-OS3 in biological samples, which kit comprises the PCR primers having the nucleotide sequence of SEQ ID NO: 5 and SEQ ID NO: 6 and the specific probe having the nucleotide sequence of SEQ ID NO: 24 for use in the GAT-OS3 (real time) PCR identification protocol described herein.

According to another aspect of the invention, DNA sequences are disclosed comprising the insertion site of the event and sufficient length of polynucleotides of both the rice genomic DNA and the foreign DNA (transgene), so as to be useful as primer or probe for the detection of GAT-OS3. Such sequences may comprise at least 9 nucleotides of the rice genomic DNA and a similar number of nucleotides of the foreign DNA (transgene) of GAT-OS3 contiguous therewith at each side of the insertion site respectively. Most preferably, such DNA sequences comprise at least 9 nucleotides of the rice genomic DNA and a similar number of nucleotides of the foreign DNA contiguous with the insertion site in SEQ ID NO: 1 or SEQ ID NO: 2.

The methods and kits encompassed by the present invention can be used for different purposes such as, but not limited to the following: to identify the presence or absence of GAT-OS3 in plants, plant material or in products such as, but not limited to food or feed products (fresh or processed) comprising or derived from plant material; additionally or alternatively, the methods and kits of the present invention can be used to identify transgenic plant material for purposes of segregation between transgenic and non-transgenic material; additionally or alternatively, the methods and kits of the present invention can be used to determine the quality (i.e. percentage pure material) of plant material comprising GAT-OS3.

The invention further relates to the 5' and/or 3' flanking regions of GAT-OS3 as well as to the specific primers and probes developed from the 5' and/or 3' flanking sequences of GAT-OS3.

The invention also relates to genomic DNA obtained from plants comprising elite event GAT-OS3. Such genomic DNA may be used as reference control material in the identification assays herein described.

The present invention further relates to a method for tracking plants comprising elite event GAT-OS3 in their genome upon introduction into another germplasm.

The invention further relates to a process for cultivating rice plants of the invention as described above, more particularly a process which comprises applying a herbicide with glufosinate as an active ingredient to the cultivated rice plants.

It is believed that the rice plants of the invention, when cultivated according to the process described above, which comprises applying a herbicide with glufosinate as an active ingredient, display improved growth as compared to untransformed rice of the same cultivar (U.S. Pat. No. 5,739,082).

The invention also provides a process for breeding rice, which comprises a crossing with the rice plants of the invention.

It will be understood that particular embodiments of the invention are described by the dependent claims cited herein.

BRIEF DESCRIPTION OF THE DRAWINGS

The following Examples, not intended to limit the invention to specific embodiments described, may be understood in conjunction with the accompanying Figures, incorporated herein by reference, in which.

DETAILED DESCRIPTION OF THE INVENTION

Figure 1:
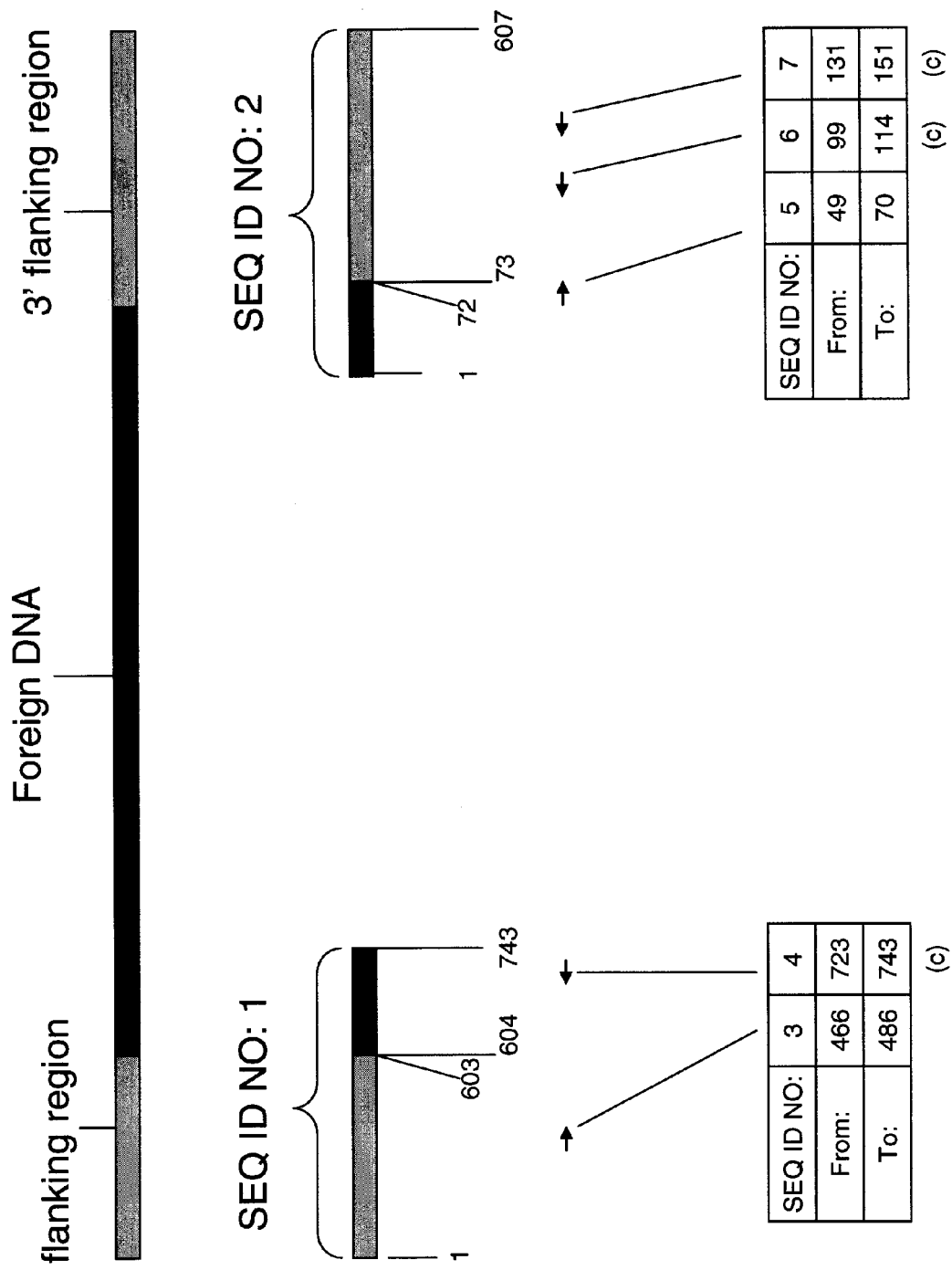
FIG. 1 represents schematically the relationship between the cited nucleotide sequences and primers. black bar: foreign DNA; light bar: DNA of plant origin; the figures under the bars represent nucleotide positions; (c) refers to complement of the indicated nucleotide sequence.

The incorporation of a recombinant DNA molecule in the plant genome typically results from transformation of a cell or tissue. The particular site of incorporation is usually due to "random" integration.

The DNA introduced into the plant genome as a result of transformation of a plant cell or tissue with a recombinant DNA or "transforming DNA," and originating from such transforming DNA is hereinafter referred to as "foreign DNA" comprising one or more "transgenes." "Plant DNA" in the context of the present invention will refer to DNA originating from the plant which is transformed. Plant DNA will usually be found in the same genetic locus in the corresponding wild-type plant. The foreign DNA can be characterized by the location and the configuration at the site of incorporation of the recombinant DNA molecule in the plant genome. The site in the plant genome where a recombinant DNA has been inserted is also referred to as the "insertion site" or "target site." Insertion of the recombinant DNA into the region of the plant genome referred to as "pre-insertion plant DNA" can be associated with a deletion of plant DNA, referred to as "target site deletion". A "flanking region" or "flanking sequence" as used herein refers to a sequence of at least 20 bp, preferably at least 50 bp, and up to 5000 bp of DNA different from the introduced DNA, preferably DNA from the plant genome which is located either immediately upstream of and contiguous with or immediately downstream of and contiguous with the foreign DNA. Transformation procedures leading to random integration of the foreign DNA will result in transformants with different flanking regions, which are characteristic and unique for each transformant. When the recombinant DNA is introduced into a plant through traditional crossing, its insertion site in the plant genome, or its flanking regions will generally not be changed. An "insertion region" as used herein refers to the region corresponding to the region of at least 40 bp, preferably at least 100 bp, and up to 10000 bp, encompassed by the sequence which comprises the upstream and/or the downstream flanking region of a foreign DNA in the plant genome. Taking into consideration minor differences due to mutations within a species, an insertion region will retain, upon crossing into a plant of the same species, at least 85%, preferably 90%, more preferably 95%, and most preferably 100% sequence identity with the sequence comprising the upstream and downstream flanking regions of the foreign DNA in the plant originally obtained from transformation.

An "event" is defined as an (artificial) genetic locus that, as a result of genetic engineering, carries a transgene comprising at least one copy of a gene of interest. The typical allelic states of an event are the presence or absence of the foreign DNA. An event is characterized phenotypically by the expression of the transgene. At the genetic level, an event is part of the genetic make-up of a plant. At the molecular level, an event can be characterized by the restriction map (e.g. as determined by Southern blotting), by the upstream and/or downstream flanking sequences of the transgene, the location of molecular markers and/or the molecular configuration of the transgene. Usually transformation of a plant with a transforming DNA comprising at least one gene of interest leads to a population of transformants comprising a multitude of separate events, each of which is unique.

An "elite event" as used herein, is an event which is selected from a group of events, obtained by transformation with the same transforming DNA or by back-crossing with plants obtained by such transformation, based on the expression and stability of the transgene(s) and its compatibility with optimal agronomic characteristics of the plant comprising it. Thus the criteria for elite event selection are one or more, preferably two or more, advantageously all of the following:
a) that the presence of the foreign DNA does not compromise other desired characteristics of the plant, such as those relating to agronomic performance or commercial value;
b) that the event is characterized by a well defined molecular configuration which is stably inherited and for which appropriate tools for identity control can be developed;
c) that the gene(s) of interest show(s) a correct, appropriate and stable spatial and temporal phenotypic expression, both in heterozygous (or hemizygous) and homozygous condition of the event, at a commercially acceptable level in a range of environmental conditions in which the plants carrying the event are likely to be exposed in normal agronomic use.

It is preferred that the foreign DNA is associated with a position in the plant genome that allows easy introgression into desired commercial genetic backgrounds.

The status of an event as an elite event is confirmed by introgression of the elite event in different relevant genetic backgrounds and observing compliance with one, two or all of the criteria e.g. a), b) and c) above.

An "elite event" thus refers to a genetic locus comprising a foreign DNA, which answers to the above-described criteria. A plant, plant material or progeny such as seeds can comprise one or more elite events in its genome.

The tools developed to identify an elite event or the plant, plant material comprising an elite event, or products which comprise plant material comprising the elite event are based on the specific genomic characteristics of the elite event, such as, a specific restriction map of the genomic region comprising the foreign DNA, molecular markers or the sequence of the flanking region(s) of the foreign DNA.

Once one or both of the flanking regions of the foreign DNA have been sequenced, primers and probes can be developed which specifically recognize this (these) sequence(s) in the nucleic acid (DNA or RNA) of a sample by way of a molecular biological technique. For instance a PCR method can be developed to identify the elite event in biological samples (such as samples of plants, plant material or products comprising plant material). Such a PCR is based on at least two specific "primers" one recognizing a sequence within the 5' or 3' flanking region of the elite event and the other recognizing a sequence within the foreign DNA. The primers preferably have a sequence of between 15 and 35 nucleotides which under optimized PCR conditions "specifically recognize" a sequence within the 5' or 3' flanking region of the elite event and the foreign DNA of the elite event respectively, so that a specific fragment ("integration fragment" or "discriminating amplicon") is amplified from a nucleic acid sample comprising the elite event. This means that only the targeted integration fragment, and no other sequence in the plant genome or foreign DNA, is amplified under optimized PCR conditions.

PCR primers suitable for the invention may be the following:
oligonucleotides ranging in length from 17 nt to about 200 nt, comprising a nucleotide sequence of at least 17 consecutive nucleotides, preferably 20 consecutive nucleotides, selected from the 5' flanking sequence (SEQ ID NO: 1 from nucleotide 1 to nucleotide 603) at their 3' end (primers recognizing 5' flanking sequences); or
oligonucleotides ranging in length from 17 nt to about 200 nt, comprising a nucleotide sequence of at least 17 consecutive nucleotides, preferably 20 consecutive nucleotides, selected from the 3' flanking sequence (complement of SEQ ID NO: 2 from nucleotide 73 to nucleotide 607) at their 3' end (primers recognizing 3' flanking sequences); or
oligonucleotides ranging in length from 17 nt to about 200 nt, comprising a nucleotide sequence of at least 17 consecutive nucleotides, preferably 20 nucleotides, selected from the inserted DNA sequences (complement of SEQ ID NO: 1 from nucleotide 604 to nucleotide 743) at their 3' end (primers recognizing foreign DNA) or
oligonucleotides ranging in length from 17 nt to about 200 nt, comprising a nucleotide sequence of at least 17 consecutive nucleotides, preferably 20 nucleotides, selected from the inserted DNA sequences (SEQ ID NO: 2 from nucleotide 1 to nucleotide 72) at their 3' end (primers recognizing foreign DNA).

The primers may of course be longer than the mentioned 17 consecutive nucleotides, and may e.g. be 20, 21, 22, 23, 30, 35, 50, 75, 100, 150, 200 nt long or even longer. The primers may entirely consist of nucleotide sequence selected from the mentioned nucleotide sequences of flanking sequences and foreign DNA sequences. However, the nucleotide sequence of the primers at their 5' end (i.e. outside of the 3'-located 17 consecutive nucleotides) is less critical. Thus, the 5' sequence of the primers may consist of a nucleotide sequence selected from the flanking sequences or foreign DNA, as appropriate, but may contain several (e.g. 1, 2, 5, 10) mismatches. The 5' sequence of the primers may even entirely consist of a nucleotide sequence unrelated to the flanking sequences or foreign DNA, such as e.g. a nucleotide sequence representing restriction enzyme recognition sites. Such unrelated sequences or flanking DNA sequences with mismatches should preferably be not longer than 100, more preferably not longer than 50 or even 25 nucleotides.

Moreover, suitable primers may comprise or consist of a nucleotide sequence at their 3' end spanning the joining region between the plant DNA derived sequences and the foreign DNA sequences (located at nucleotides 603-604 in SEQ ID NO: 1 and nucleotides 72-73 in SEQ ID NO: 2) provided the mentioned 3'-located 17 consecutive nucleotides are not derived exclusively from either the foreign DNA or plant-derived sequences in SEQ ID NO: 1 or 2.

It will also be immediately clear to the skilled artisan that properly selected PCR primer pairs should also not comprise sequences complementary to each other.

For the purpose of the invention, the "complement of a nucleotide sequence represented in SEQ ID NO: X" is the nucleotide sequence which can be derived from the represented nucleotide sequence by replacing the nucleotides through their complementary nucleotide according to Chargaff's rules (A⇔T; G⇔C) and reading the sequence in the 5' to 3' direction, i.e., in opposite direction of the represented nucleotide sequence.

Examples of suitable primers are the oligonucleotide sequences of SEQ ID NO: 3 (5' flanking sequence recognizing primer), SEQ ID NO: 4 (foreign DNA recognizing primer for use with 5' flanking sequence recognizing primer), SEQ ID NO: 5 (foreign DNA recognizing primer for use with 3' flanking sequence recognizing primer), or SEQ ID NO: 6, and SEQ ID NO: 7 (3' flanking sequence recognizing primer).

Other examples of suitable oligonucleotide primers comprise at their 3' end the following sequences or consist of such sequences:

a. 5' flanking sequence recognizing primers:
    the nucleotide sequence of SEQ ID NO: 1 from nucleotide 362 to nucleotide 381
    the nucleotide sequence of SEQ ID NO: 1 from nucleotide 358 to nucleotide 377
    the nucleotide sequence of SEQ ID NO: 1 from nucleotide 363 to nucleotide 382
    the nucleotide sequence of SEQ ID NO: 1 from nucleotide 359 to nucleotide 377
    the nucleotide sequence of SEQ ID NO: 1 from nucleotide 362 to nucleotide 382
    the nucleotide sequence of SEQ ID NO: 1 from nucleotide 360 to nucleotide 377
    the nucleotide sequence of SEQ ID NO: 1 from nucleotide 361 to nucleotide 382
    the nucleotide sequence of SEQ ID NO: 1 from nucleotide 365 to nucleotide 382
    the nucleotide sequence of SEQ ID NO: 1 from nucleotide 361 to nucleotide 377
    the nucleotide sequence of SEQ ID NO: 1 from nucleotide 366 to nucleotide 382
    the nucleotide sequence of SEQ ID NO: 1 from nucleotide 469 to nucleotide 485
    the nucleotide sequence of SEQ ID NO: 1 from nucleotide 468 to nucleotide 485
    the nucleotide sequence of SEQ ID NO: 1 from nucleotide 468 to nucleotide 486
    the nucleotide sequence of SEQ ID NO: 1 from nucleotide 470 to nucleotide 486
    the nucleotide sequence of SEQ ID NO: 1 from nucleotide 484 to nucleotide 500
    the nucleotide sequence of SEQ ID NO: 1 from nucleotide 596 to nucleotide 612
    the nucleotide sequence of SEQ ID NO: 1 from nucleotide 441 to nucleotide 457 b. foreign DNA sequence recognizing primers for use with 5' flanking sequence recognizing primers:
    the complement of the nucleotide sequence of SEQ ID NO: 1 from nucleotide 684 to 701
    the complement of the nucleotide sequence of SEQ ID NO: 1 from nucleotide 684 to 703
    the complement of the nucleotide sequence of SEQ ID NO: 1 from nucleotide 661 to 680
    the complement of the nucleotide sequence of SEQ ID NO: 1 from nucleotide 679 to 698
    the complement of the nucleotide sequence of SEQ ID NO: 1 from nucleotide 684 to 700
    the complement of the nucleotide sequence of SEQ ID NO: 1 from nucleotide 679 to 699
    the complement of the nucleotide sequence of SEQ ID NO: 1 from nucleotide 689 to 710
    the complement of the nucleotide sequence of SEQ ID NO: 1 from nucleotide 661 to 682
    the complement of the nucleotide sequence of SEQ ID NO: 1 from nucleotide 679 to 700
    the complement of the nucleotide sequence of SEQ ID NO: 1 from nucleotide 679 to 701
    the complement of the nucleotide sequence of SEQ ID NO: 1 from nucleotide 671 to 689
    the complement of the nucleotide sequence of SEQ ID NO: 1 from nucleotide 671 to 690
    the complement of the nucleotide sequence of SEQ ID NO: 1 from nucleotide 671 to 687
    the complement of the nucleotide sequence of SEQ ID NO: 1 from nucleotide 671 to 688
    the complement of the nucleotide sequence of SEQ ID NO: 1 from nucleotide 671 to 691
    the complement of the nucleotide sequence of SEQ ID NO: 1 from nucleotide 671 to 692
    the complement of the nucleotide sequence of SEQ ID NO: 1 from nucleotide 671 to 693 c. 3' flanking sequence recognizing primers:
    the complement of the nucleotide sequence of SEQ ID NO: 2 from nucleotide 381 to 400
    the complement of the nucleotide sequence of SEQ ID NO: 2 from nucleotide 383 to 402
    the complement of the nucleotide sequence of SEQ ID NO: 2 from nucleotide 381 to 399
    the complement of the nucleotide sequence of SEQ ID NO: 2 from nucleotide 380 to 399
    the complement of the nucleotide sequence of SEQ ID NO: 2 from nucleotide 381 to 401
    the complement of the nucleotide sequence of SEQ ID NO: 2 from nucleotide 383 to 401
    the complement of the nucleotide sequence of SEQ ID NO: 2 from nucleotide 383 to 403
    the complement of the nucleotide sequence of SEQ ID NO: 2 from nucleotide 435 to 454
    the complement of the nucleotide sequence of SEQ ID NO: 2 from nucleotide 501 to 520
    the complement of the nucleotide sequence of SEQ ID NO: 2 from nucleotide 506 to 525
    the complement of the nucleotide sequence of SEQ ID NO: 2 from nucleotide 507 to 526
    the complement of the nucleotide sequence of SEQ ID NO: 2 from nucleotide 63 to 82
    the complement of the nucleotide sequence of SEQ ID NO: 2 from nucleotide 186 to 205
    the complement of the nucleotide sequence of SEQ ID NO: 2 from nucleotide 188 to 207
    the complement of the nucleotide sequence of SEQ ID NO: 2 from nucleotide 344 to 363 the complement of the nucleotide sequence of SEQ ID NO: 2 from nucleotide 381 to 398
the complement of the nucleotide sequence of SEQ ID NO: 2 from nucleotide 380 to 400
the complement of the nucleotide sequence of SEQ ID NO: 2 from nucleotide 383 to 400
the complement of the nucleotide sequence of SEQ ID NO: 2 from nucleotide 381 to 402
the complement of the nucleotide sequence of SEQ ID NO: 2 from nucleotide 383 to 404
the complement of the nucleotide sequence of SEQ ID NO: 2 from nucleotide 435 to 453
the complement of the nucleotide sequence of SEQ ID NO: 2 from nucleotide 434 to 453
the complement of the nucleotide sequence of SEQ ID NO: 2 from nucleotide 491 to 510
the complement of the nucleotide sequence of SEQ ID NO: 2 from nucleotide 492 to 511
the complement of the nucleotide sequence of SEQ ID NO: 2 from nucleotide 494 to 513
the complement of the nucleotide sequence of SEQ ID NO: 2 from nucleotide 501 to 519
the complement of the nucleotide sequence of SEQ ID NO: 2 from nucleotide 502 to 520
the complement of the nucleotide sequence of SEQ ID NO: 2 from nucleotide 502 to 521
the complement of the nucleotide sequence of SEQ ID NO: 2 from nucleotide 506 to 524
the complement of the nucleotide sequence of SEQ ID NO: 2 from nucleotide 507 to 525
the complement of the nucleotide sequence of SEQ ID NO: 2 from nucleotide 507 to 527
the complement of the nucleotide sequence of SEQ ID NO: 2 from nucleotide 568 to 587
the complement of the nucleotide sequence of SEQ ID NO: 2 from nucleotide 586 to 603
the complement of the nucleotide sequence of SEQ ID NO: 2 from nucleotide 63 to 81
the complement of the nucleotide sequence of SEQ ID NO: 2 from nucleotide 63 to 83
the complement of the nucleotide sequence of SEQ ID NO: 2 from nucleotide 183 to 199
the complement of the nucleotide sequence of SEQ ID NO: 2 from nucleotide 183 to 202
the complement of the nucleotide sequence of SEQ ID NO: 2 from nucleotide 188 to 206
the complement of the nucleotide sequence of SEQ ID NO: 2 from nucleotide 186 to 206
the complement of the nucleotide sequence of SEQ ID NO: 2 from nucleotide 188 to 208
the complement of the nucleotide sequence of SEQ ID NO: 2 from nucleotide 203 to 219
the complement of the nucleotide sequence of SEQ ID NO: 2 from nucleotide 249 to 268
the complement of the nucleotide sequence of SEQ ID NO: 2 from nucleotide 251 to 270
the complement of the nucleotide sequence of SEQ ID NO: 2 from nucleotide 253 to 272
the complement of the nucleotide sequence of SEQ ID NO: 2 from nucleotide 383 to 399
the complement of the nucleotide sequence of SEQ ID NO: 2 from nucleotide 380 to 401
the complement of the nucleotide sequence of SEQ ID NO: 2 from nucleotide 381 to 403
the complement of the nucleotide sequence of SEQ ID NO: 2 from nucleotide 383 to 405
the complement of the nucleotide sequence of SEQ ID NO: 2 from nucleotide 434 to 452
the complement of the nucleotide sequence of SEQ ID NO: 2 from nucleotide 435 to 452
the complement of the nucleotide sequence of SEQ ID NO: 2 from nucleotide 492 to 510
the complement of the nucleotide sequence of SEQ ID NO: 2 from nucleotide 494 to 512
the complement of the nucleotide sequence of SEQ ID NO: 2 from nucleotide 492 to 512
the complement of the nucleotide sequence of SEQ ID NO: 2 from nucleotide 494 to 514
the complement of the nucleotide sequence of SEQ ID NO: 2 from nucleotide 501 to 518
the complement of the nucleotide sequence of SEQ ID NO: 2 from nucleotide 502 to 519
the complement of the nucleotide sequence of SEQ ID NO: 2 from nucleotide 501 to 521
the complement of the nucleotide sequence of SEQ ID NO: 2 from nucleotide 502 to 522
the complement of the nucleotide sequence of SEQ ID NO: 2 from nucleotide 507 to 524
the complement of the nucleotide sequence of SEQ ID NO: 2 from nucleotide 506 to 527
the complement of the nucleotide sequence of SEQ ID NO: 2 from nucleotide 507 to 528
the complement of the nucleotide sequence of SEQ ID NO: 2 from nucleotide 568 to 586
the complement of the nucleotide sequence of SEQ ID NO: 2 from nucleotide 568 to 588
the complement of the nucleotide sequence of SEQ ID NO: 2 from nucleotide 586 to 602
the complement of the nucleotide sequence of SEQ ID NO: 2 from nucleotide 63 to 84
the complement of the nucleotide sequence of SEQ ID NO: 2 from nucleotide 177 to 193
the complement of the nucleotide sequence of SEQ ID NO: 2 from nucleotide 177 to 199
the complement of the nucleotide sequence of SEQ ID NO: 2 from nucleotide 183 to 201
the complement of the nucleotide sequence of SEQ ID NO: 2 from nucleotide 186 to 207
the complement of the nucleotide sequence of SEQ ID NO: 2 from nucleotide 188 to 209
the complement of the nucleotide sequence of SEQ ID NO: 2 from nucleotide 203 to 220
the complement of the nucleotide sequence of SEQ ID NO: 2 from nucleotide 203 to 222
the complement of the nucleotide sequence of SEQ ID NO: 2 from nucleotide 204 to 223
the complement of the nucleotide sequence of SEQ ID NO: 2 from nucleotide 249 to 267
the complement of the nucleotide sequence of SEQ ID NO: 2 from nucleotide 251 to 269
the complement of the nucleotide sequence of SEQ ID NO: 2 from nucleotide 249 to 269
the complement of the nucleotide sequence of SEQ ID NO: 2 from nucleotide 251 to 271
the complement of the nucleotide sequence of SEQ ID NO: 2 from nucleotide 253 to 271
the complement of the nucleotide sequence of SEQ ID NO: 2 from nucleotide 380 to 402 the complement of the nucleotide sequence of SEQ ID NO: 2 from nucleotide 435 to 451
the complement of the nucleotide sequence of SEQ ID NO: 2 from nucleotide 434 to 451
the complement of the nucleotide sequence of SEQ ID NO: 2 from nucleotide 437 to 453
the complement of the nucleotide sequence of SEQ ID NO: 2 from nucleotide 491 to 512
the complement of the nucleotide sequence of SEQ ID NO: 2 from nucleotide 492 to 513
the complement of the nucleotide sequence of SEQ ID NO: 2 from nucleotide 494 to 515
the complement of the nucleotide sequence of SEQ ID NO: 2 from nucleotide 502 to 518
the complement of the nucleotide sequence of SEQ ID NO: 2 from nucleotide 501 to 522
the complement of the nucleotide sequence of SEQ ID NO: 2 from nucleotide 506 to 522
the complement of the nucleotide sequence of SEQ ID NO: 2 from nucleotide 507 to 523
the complement of the nucleotide sequence of SEQ ID NO: 2 from nucleotide 506 to 528
the complement of the nucleotide sequence of SEQ ID NO: 2 from nucleotide 507 to 529
the complement of the nucleotide sequence of SEQ ID NO: 2 from nucleotide 568 to 585
the complement of the nucleotide sequence of SEQ ID NO: 2 from nucleotide 568 to 589
the complement of the nucleotide sequence of SEQ ID NO: 2 from nucleotide 63 to 79
the complement of the nucleotide sequence of SEQ ID NO: 2 from nucleotide 63 to 85
the complement of the nucleotide sequence of SEQ ID NO: 2 from nucleotide 127 to 146
the complement of the nucleotide sequence of SEQ ID NO: 2 from nucleotide 186 to 202
the complement of the nucleotide sequence of SEQ ID NO: 2 from nucleotide 186 to 208
the complement of the nucleotide sequence of SEQ ID NO: 2 from nucleotide 188 to 210
the complement of the nucleotide sequence of SEQ ID NO: 2 from nucleotide 203 to 221
the complement of the nucleotide sequence of SEQ ID NO: 2 from nucleotide 204 to 222
the complement of the nucleotide sequence of SEQ ID NO: 2 from nucleotide 204 to 224
the complement of the nucleotide sequence of SEQ ID NO: 2 from nucleotide 227 to 246
the complement of the nucleotide sequence of SEQ ID NO: 2 from nucleotide 229 to 248
the complement of the nucleotide sequence of SEQ ID NO: 2 from nucleotide 249 to 266
the complement of the nucleotide sequence of SEQ ID NO: 2 from nucleotide 249 to 270
the complement of the nucleotide sequence of SEQ ID NO: 2 from nucleotide 253 to 270
the complement of the nucleotide sequence of SEQ ID NO: 2 from nucleotide 251 to 272
the complement of the nucleotide sequence of SEQ ID NO: 2 from nucleotide 434 to 450
the complement of the nucleotide sequence of SEQ ID NO: 2 from nucleotide 494 to 510
the complement of the nucleotide sequence of SEQ ID NO: 2 from nucleotide 491 to 513
the complement of the nucleotide sequence of SEQ ID NO: 2 from nucleotide 492 to 514
the complement of the nucleotide sequence of SEQ ID NO: 2 from nucleotide 494 to 516
the complement of the nucleotide sequence of SEQ ID NO: 2 from nucleotide 501 to 523
the complement of the nucleotide sequence of SEQ ID NO: 2 from nucleotide 511 to 533
the complement of the nucleotide sequence of SEQ ID NO: 2 from nucleotide 568 to 590
the complement of the nucleotide sequence of SEQ ID NO: 2 from nucleotide 127 to 145
the complement of the nucleotide sequence of SEQ ID NO: 2 from nucleotide 127 to 147
the complement of the nucleotide sequence of SEQ ID NO: 2 from nucleotide 183 to 205
the complement of the nucleotide sequence of SEQ ID NO: 2 from nucleotide 185 to 206
the complement of the nucleotide sequence of SEQ ID NO: 2 from nucleotide 204 to 221
the complement of the nucleotide sequence of SEQ ID NO: 2 from nucleotide 203 to 223
the complement of the nucleotide sequence of SEQ ID NO: 2 from nucleotide 204 to 225
the complement of the nucleotide sequence of SEQ ID NO: 2 from nucleotide 227 to 245
the complement of the nucleotide sequence of SEQ ID NO: 2 from nucleotide 249 to 265
the complement of the nucleotide sequence of SEQ ID NO: 2 from nucleotide 251 to 267
the complement of the nucleotide sequence of SEQ ID NO: 2 from nucleotide 246 to 268
the complement of the nucleotide sequence of SEQ ID NO: 2 from nucleotide 253 to 269
the complement of the nucleotide sequence of SEQ ID NO: 2 from nucleotide 249 to 271
the complement of the nucleotide sequence of SEQ ID NO: 2 from nucleotide 255 to 271
the complement of the nucleotide sequence of SEQ ID NO: 2 from nucleotide 251 to 273
the complement of the nucleotide sequence of SEQ ID NO: 2 from nucleotide 253 to 275
the complement of the nucleotide sequence of SEQ ID NO: 2 from nucleotide 127 to 144
the complement of the nucleotide sequence of SEQ ID NO: 2 from nucleotide 185 to 201
the complement of the nucleotide sequence of SEQ ID NO: 2 from nucleotide 185 to 207
the complement of the nucleotide sequence of SEQ ID NO: 2 from nucleotide 202 to 223
the complement of the nucleotide sequence of SEQ ID NO: 2 from nucleotide 203 to 224
the complement of the nucleotide sequence of SEQ ID NO: 2 from nucleotide 227 to 248
the complement of the nucleotide sequence of SEQ ID NO: 2 from nucleotide 229 to 250
the complement of the nucleotide sequence of SEQ ID NO: 2 from nucleotide 127 to 143
the complement of the nucleotide sequence of SEQ ID NO: 2 from nucleotide 202 to 224
the complement of the nucleotide sequence of SEQ ID NO: 2 from nucleotide 203 to 225
the complement of the nucleotide sequence of SEQ ID NO: 2 from nucleotide 227 to 243 the complement of the nucleotide sequence of SEQ ID NO: 2 from nucleotide 229 to 245
the complement of the nucleotide sequence of SEQ ID NO: 2 from nucleotide 227 to 249
the complement of the nucleotide sequence of SEQ ID NO: 2 from nucleotide 229 to 251
the complement of the nucleotide sequence of SEQ ID NO: 2 from nucleotide 234 to 256
the complement of the nucleotide sequence of SEQ ID NO: 2 from nucleotide 585 to 604
the complement of the nucleotide sequence of SEQ ID NO: 2 from nucleotide 127 to 148
the complement of the nucleotide sequence of SEQ ID NO: 2 from nucleotide 353 to 375
the complement of the nucleotide sequence of SEQ ID NO: 2 from nucleotide 504 to 523
the complement of the nucleotide sequence of SEQ ID NO: 2 from nucleotide 585 to 603
the complement of the nucleotide sequence of SEQ ID NO: 2 from nucleotide 504 to 522
the complement of the nucleotide sequence of SEQ ID NO: 2 from nucleotide 504 to 524
the complement of the nucleotide sequence of SEQ ID NO: 2 from nucleotide 585 to 602
the complement of the nucleotide sequence of SEQ ID NO: 2 from nucleotide 504 to 520
the complement of the nucleotide sequence of SEQ ID NO: 2 from nucleotide 504 to 521
the complement of the nucleotide sequence of SEQ ID NO: 2 from nucleotide 504 to 525
the complement of the nucleotide sequence of SEQ ID NO: 2 from nucleotide 585 to 601
the complement of the nucleotide sequence of SEQ ID NO: 2 from nucleotide 268 to 284
the complement of the nucleotide sequence of SEQ ID NO: 2 from nucleotide 504 to 526
the complement of the nucleotide sequence of SEQ ID NO: 2 from nucleotide 574 to 593
the complement of the nucleotide sequence of SEQ ID NO: 2 from nucleotide 581 to 600
the complement of the nucleotide sequence of SEQ ID NO: 2 from nucleotide 574 to 592
the complement of the nucleotide sequence of SEQ ID NO: 2 from nucleotide 581 to 601
the complement of the nucleotide sequence of SEQ ID NO: 2 from nucleotide 581 to 602
the complement of the nucleotide sequence of SEQ ID NO: 2 from nucleotide 574 to 596
the complement of the nucleotide sequence of SEQ ID NO: 2 from nucleotide 581 to 603 d. foreign DNA sequence recognizing primers for use with 3' flanking sequence recognizing primers:

the nucleotide sequence of SEQ ID NO: 2 from nucleotide 25 to nucleotide 44
the nucleotide sequence of SEQ ID NO: 2 from nucleotide 35 to nucleotide 54
the nucleotide sequence of SEQ ID NO: 2 from nucleotide 24 to nucleotide 44
the nucleotide sequence of SEQ ID NO: 2 from nucleotide 26 to nucleotide 44
the nucleotide sequence of SEQ ID NO: 2 from nucleotide 34 to nucleotide 54
the nucleotide sequence of SEQ ID NO: 2 from nucleotide 36 to nucleotide 54
the nucleotide sequence of SEQ ID NO: 2 from nucleotide 40 to nucleotide 59
the nucleotide sequence of SEQ ID NO: 2 from nucleotide 43 to nucleotide 62
the nucleotide sequence of SEQ ID NO: 2 from nucleotide 27 to nucleotide 44
the nucleotide sequence of SEQ ID NO: 2 from nucleotide 33 to nucleotide 54
the nucleotide sequence of SEQ ID NO: 2 from nucleotide 37 to nucleotide 54
the nucleotide sequence of SEQ ID NO: 2 from nucleotide 39 to nucleotide 59
the nucleotide sequence of SEQ ID NO: 2 from nucleotide 41 to nucleotide 59
the nucleotide sequence of SEQ ID NO: 2 from nucleotide 42 to nucleotide 62
the nucleotide sequence of SEQ ID NO: 2 from nucleotide 44 to nucleotide 62
the nucleotide sequence of SEQ ID NO: 2 from nucleotide 23 to nucleotide 44
the nucleotide sequence of SEQ ID NO: 2 from nucleotide 32 to nucleotide 54
the nucleotide sequence of SEQ ID NO: 2 from nucleotide 38 to nucleotide 59
the nucleotide sequence of SEQ ID NO: 2 from nucleotide 38 to nucleotide 54
the nucleotide sequence of SEQ ID NO: 2 from nucleotide 41 to nucleotide 62
the nucleotide sequence of SEQ ID NO: 2 from nucleotide 44 to nucleotide 65
the nucleotide sequence of SEQ ID NO: 2 from nucleotide 22 to nucleotide 44
the nucleotide sequence of SEQ ID NO: 2 from nucleotide 23 to nucleotide 39
the nucleotide sequence of SEQ ID NO: 2 from nucleotide 37 to nucleotide 59
the nucleotide sequence of SEQ ID NO: 2 from nucleotide 40 to nucleotide 62
the nucleotide sequence of SEQ ID NO: 2 from nucleotide 43 to nucleotide 65
the nucleotide sequence of SEQ ID NO: 2 from nucleotide 43 to nucleotide 59
the nucleotide sequence of SEQ ID NO: 2 from nucleotide 44 to nucleotide 63
the nucleotide sequence of SEQ ID NO: 2 from nucleotide 43 to nucleotide 63
the nucleotide sequence of SEQ ID NO: 2 from nucleotide 42 to nucleotide 63
the nucleotide sequence of SEQ ID NO: 2 from nucleotide 41 to nucleotide 63

As used herein, "the nucleotide sequence of SEQ ID NO: Z from nucleotide X to (nucleotide) Y" indicates the nucleotide sequence including both nucleotide endpoints.

Preferably, the integration fragment or discriminating amplicon has a length of between 50 and 500 nucleotides, such as a length of between 100 and 350 nucleotides. The specific primers may have a sequence which is between 80 and 100% identical to a sequence within the 5' or 3' flanking region of the elite event and the foreign DNA of the elite event, respectively, provided the mismatches still allow specific identification of the elite event with these primers under optimized PCR conditions. The range of allowable mismatches however, can easily be determined experimentally and are known to a person skilled in the art.

The following table exemplifies the sizes of expected DNA amplicons (or integration fragments) with selected pairs of PCR primers.

| Primer 1 | From position | Primer 2 | To position | Length amplicon |
|---|---|---|---|---|
| OSA010 (SEQ ID NO: 3) | 466 in SEQ ID NO: 1 | OSA009 (SEQ ID NO: 4) | 743 in SEQ ID NO: 1 | 278 |
| SHA040 (SEQ ID NO: 5) | 49 in SEQ ID NO: 2 | SHA041 (SEQ ID NO: 6) | 114 in SEQ ID NO: 2 | 66 |
| SHA040 (SEQ ID NO: 5) | 49 in SEQ ID NO: 2 | YTP172 (SEQ ID NO: 7) | 151 in SEQ ID NO: 2 | 103 |

Detection of integration fragments or discriminating amplicons can occur in various ways e.g. via size estimation after gel analysis or via measurement of fluorescence signals produced by a fluorescent-labeled probe, capable of hybridizing to the target sequence spanned by the primers, upon release from the template DNA at each PCR cycle. The integration fragments may also be directly sequenced. Other sequence specific methods for detection of amplified DNA fragments are also known in the art.

As the sequence of the primers and their relative location in the genome are unique for the elite event, amplification of the integration fragment will occur only in biological samples comprising (the nucleic acid of) the elite event. Preferably when performing a PCR to identify the presence of GAT-OS3 in unknown samples, a control is included of a set of primers with which a fragment within a "housekeeping gene" of the plant species of the event can be amplified. Housekeeping genes are genes that are expressed in most cell types and which are concerned with basic metabolic activities common to all cells. Preferably, the fragment amplified from the housekeeping gene is a fragment which is larger than the amplified integration fragment and/or the fluorescent-labeled probe specific for the target sequence spanned by the primers amplifying the fragment from the housekeeping gene is labeled with a fluorescent different from the fluorescent with which the probe specific for the target sequence spanned by the primers amplifying the integration fragment is labeled. Depending on the samples to be analyzed, other controls can be included.

Standard PCR protocols are described in the art, such as in "PCR Applications Manual" (Roche Molecular Biochemicals, 2nd Edition, 1999) and other references. The optimal conditions for the (real time) PCR, including the sequence of the specific primers, is specified in a "(real time) PCR identification protocol" for each elite event. It is however understood that a number of parameters in the PCR identification protocol may need to be adjusted to specific laboratory conditions, and may be modified slightly to obtain similar results. For instance, use of a different method for preparation of DNA may require adjustment of, for instance, the amount of primers, polymerase and annealing conditions used. Similarly, the selection of other primers may dictate other optimal conditions for the PCR identification protocol. These adjustments will however be apparent to a person skilled in the art, and are furthermore detailed in current PCR application manuals such as the one cited above.

Alternatively, specific primers can be used to amplify an integration fragment that can be used as a "specific probe" for identifying GAT-OS3 in biological samples. Contacting nucleic acid of a biological sample, with the probe, under conditions which allow hybridization of the probe with its corresponding fragment in the nucleic acid, results in the formation of a nucleic acid/probe hybrid. The formation of this hybrid can be detected (e.g. labeling of the nucleic acid or probe), whereby the formation of this hybrid indicates the presence of GAT-OS3. Such identification methods based on hybridization with a specific probe (either on a solid phase carrier or in solution) have been described in the art. The specific probe is preferably a sequence which, under optimized conditions, hybridizes specifically to a region within the 5' or 3' flanking region of the elite event and preferably also comprising part of the foreign DNA contiguous therewith (hereinafter referred to as "specific region"). Preferably, the specific probe comprises a sequence of between 20 and 500 bp, preferably of 100 to 350 bp which is at least 80%, preferably between 80 and 85%, more preferably between 85 and 90%, especially preferably between 90 and 95%, most preferably between 95% and 100% identical (or complementary) to the nucleotide sequence of a specific region. Preferably, the specific probe will comprise a sequence of about 15 to about 100 contiguous nucleotides identical (or complementary) to a specific region of the elite event.

Oligonucleotides suitable as PCR primers for detection of the elite event GAT-OS3 can also be used to develop a PCR-based protocol to determine the zygosity status of the elite event. To this end, two primers recognizing the wild-type locus are designed in such a way that they are directed towards each other and have the insertion site located in between the primers. These primers may be primers specifically recognizing the 5' and 3' flanking sequences contained within SEQ ID NO: 1 or 2, respectively. These primers may also be primers specifically recognizing the 5' or 3' flanking sequence, such as a primer having the nucleotide sequence of SEQ ID NO: 3 or SEQ ID NO: 6. This set of primers, together with a third primer complementary to transforming DNA sequences and directed towards one of the flanking DNA, such as a primers having the nucleotide sequence of SEQ ID NO: 4 or SEQ ID NO: 5, allow simultaneous diagnostic PCR amplification of the GAT-OS3 specific locus, as well as of the wild-type locus. If the plant is homozygous for the transgenic locus or the corresponding wild-type locus, the diagnostic PCR will give rise to a single PCR product typical, preferably typical in length, for either the transgenic or wt locus. If the plant is hemizygous for the transgenic locus, two locus specific PCR products will appear, reflecting both the amplification of the transgenic and wt locus.

Furthermore, detection methods specific for elite event GAT-OS3 which differ from PCR based amplification methods can also be developed using the elite event specific sequence information provided herein. Such alternative detection methods include linear signal amplification detection methods based on invasive cleavage of particular nucleic acid structures, also known as Invader™ technology, (as described e.g. in U.S. Pat. No. 5,985,557 "Invasive Cleavage of Nucleic Acids", U.S. Pat. No. 6,001,567 "Detection of Nucleic Acid sequences by Invader Directed Cleavage, incorporated herein by reference). To this end, the target sequence may be hybridized with a labeled first nucleic acid oligonucleotide comprising the nucleotide sequence of SEQ ID NO: 1 from nucleotide 604 to nucleotide 620 or its complement or said labeled nucleic acid probe comprising the nucleotide sequence of SEQ ID NO: 2 from nucleotide 56 to nucleotide 72 or its complement and is further hybridized with a second nucleic acid oligonucleotide comprising the nucleotide sequence of SEQ ID NO: 1 from nucleotide 587 to nucleotide 603 or its complement or said labeled nucleic acid probe comprising the nucleotide sequence of SEQ ID NO: 2 from nucleotide 73 to nucleotide 89 or its complement, wherein the first and second oligonucleotide overlap by at least one nucleotide. The duplex or triplex structure which is produced by this hybridization allows selective probe cleavage with an enzyme (Cleavase®) leaving the target sequence intact. The cleaved labeled probe is subsequently detected, potentially via an intermediate step resulting in further signal amplification.

Identification of the protein(s) encoded by the foreign DNA of the elite event can be done by classical protein detection methods described in the art, such as those based on chromatographic or electromagnetic properties of the protein or the detection by specific monoclonal antibodies (as described in "Guide to protein purification", Murray P. Deutscher editor).

A "kit" as used herein refers to a set of reagents for the purpose of performing the method of the invention, more particularly, the identification and/or quantification of the elite event GAT-OS3 in biological samples or the determination of the zygosity status of GAT-OS3 containing plant material. More particularly, a preferred embodiment of the kit of the invention comprises at least one or two specific primers, as described above for identification of the elite event, or three specific primers for the determination of the zygosity status. Optionally, the kit can further comprise any other reagent described herein in the PCR identification protocol. Alternatively, according to another embodiment of this invention, the kit can comprise a specific probe, as described above, which specifically hybridizes with nucleic acid of biological samples to identify the presence of GAT-OS3 therein. Furthermore, according to yet another embodiment of this invention, the kit can comprise at least one or two specific primers and a specific probe, as described above for identification and/or quantification of the elite event. Optionally, the kit can further comprise any other reagent (such as but not limited to hybridizing buffer, label) for identification of GAT-OS3 in biological samples, using the specific probe.

The kit of the invention can be used, and its components can be specifically adjusted, for purposes of quality control (e.g., purity of seed lots), detection of the presence or absence of the elite event in plant material or material comprising or derived from plant material, such as but not limited to food or feed products.

As used herein, "sequence identity" with regard to nucleotide sequences (DNA or RNA), refers to the number of positions with identical nucleotides divided by the number of nucleotides in the shorter of the two sequences. The alignment of the two nucleotide sequences is performed by the Wilbur and Lipmann algorithm (Wilbur and Lipmann, 1983, Proc. Nat. Acad. Sci. USA 80:726) using a window-size of 20 nucleotides, a word length of 4 nucleotides, and a gap penalty of 4. Computer-assisted analysis and interpretation of sequence data, including sequence alignment as described above, can, e.g., be conveniently performed using the sequence analysis software package of the Genetics Computer Group (GCG, University of Wisconsin Biotechnology center). Sequences are indicated as "essentially similar" when such sequences have a sequence identity of at least about 75%, particularly at least about 80%, more particularly at least about 85%, quite particularly about 90%, especially about 95%, more especially about 100%. It is clear than when RNA sequences are said to be essentially similar or have a certain degree of sequence identity with DNA sequences, thymidine (T) in the DNA sequence is considered equal to uracil (U) in the RNA sequence.

The term "primer" as used herein encompasses any nucleic acid that is capable of priming the synthesis of a nascent nucleic acid in a template-dependent process, such as PCR. Typically, primers are oligonucleotides from 10 to 30 nucleotides, but longer sequences can be employed. Primers may be provided in double-stranded form, though the single-stranded form is preferred. Probes can be used as primers, but are designed to bind to the target DNA or RNA and need not be used in an amplification process.

The term "recognizing" as used herein when referring to specific primers, refers to the fact that the specific primers specifically hybridize to a nucleic acid sequence in the elite event under the conditions set forth in the method (such as the conditions of the PCR identification protocol or the real time PCR identification protocol), whereby the specificity is determined by the presence of positive and negative controls.

The term "hybridizing" as used herein when referring to specific probes, refers to the fact that the probe binds to a specific region in the nucleic acid sequence of the elite event under standard stringency conditions. Standard stringency conditions as used herein refers to the conditions for hybridization described herein or to the conventional hybridizing conditions as described by Sambrook et al., 1989 (Molecular Cloning: A Laboratory Manual, Second Edition, Cold Spring Harbour Laboratory Press, NY) which for instance can comprise the following steps: 1) immobilizing plant genomic DNA fragments on a filter, 2) prehybridizing the filter for 1 to 2 hours at 42° C. in 50% formamide, 5×SSPE, 2×Denhardt's reagent and 0.1% SDS, or for 1 to 2 hours at 68° C. in 6×SSC, 2×Denhardt's reagent and 0.1% SDS, 3) adding the hybridization probe which has been labeled, 4) incubating for 16 to 24 hours, 5) washing the filter for 20 min. at room temperature in 1×SSC, 0.1% SDS, 6) washing the filter three times for 20 min. each at 68° C. in 0.2×SSC, 0.1% SDS, and 7) exposing the filter for 24 to 48 hours to X-ray film at −70° C. with an intensifying screen.

As used in herein, a "biological sample" is a sample of a plant, plant material or products comprising plant material. The term "plant" is intended to encompass rice (*Oryza sativa*) plant tissues, at any stage of maturity, as well as any cells, tissues, or organs taken from or derived from any such plant, including without limitation, any seeds, leaves, stems, flowers, roots, single cells, gametes, cell cultures, tissue cultures or protoplasts. "Plant material", as used herein refers to material which is obtained or derived from a plant. Products comprising plant material relate to food, feed or other products which are produced using plant material or can be contaminated by plant material. It is understood that, in the context of the present invention, such biological samples are tested for the presence of nucleic acids specific for GAT-OS3, implying the presence of nucleic acids in the samples. Thus the methods referred to herein for identifying elite event GAT-OS3 in biological samples, relate to the identification in biological samples of nucleic acids which comprise the elite event.

As used herein "comprising" is to be interpreted as specifying the presence of the stated features, integers, steps, reagents or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA sequence, which is functionally or structurally defined, may comprise additional DNA sequences, etc.

The present invention also relates to the development of an elite event GAT-OS3 in rice to the plants comprising this event, the progeny obtained from these plants and to the plant cells, or plant material derived from this event. Plants comprising elite event GAT-OS3 were obtained through transformation as described in Example 1.

Rice plants or plant material comprising GAT-OS3 can be identified according to the PCR identification protocol described for GAT-OS3 in Example 4 or the real time PCR identification protocol described for GAT-OS3 in Example 6. Briefly, rice genomic DNA present in the biological sample is amplified by PCR using a primer which specifically recognizes a sequence within the 5' or 3' flanking sequence of GAT-OS3 such as the primer with the sequence of SEQ ID NO: 3 or SEQ ID NO: 6, respectively, and a primer which recognizes a sequence in the foreign DNA, such as the primer with the sequence of SEQ ID NO: 4 or SEQ ID NO: 5, respectively. DNA primers which amplify part of an endogenous rice sequence, such as the primer pair with the sequences of SEQ ID NO: 8 and 9 or the primer pair with the sequences of SEQ ID NO: 10 and 11, are used as positive control for the PCR amplification. If upon PCR amplification, the material yields a fragment of the expected size, the material contains plant material from a rice plant harboring elite event GAT-OS3. The production of the specific PCR fragments can, e.g., be monitored by gel analysis or by including fluorescent-labeled probes capable of hybridizing to the target sequence spanned by the primers amplifying the integration fragment of elite event GAT-OS3, such as the probe with the sequence of SEQ ID NO: 24 which is capable of hybridizing to the target sequence spanned by the primers with the sequence of SEQ ID NO: 5 and 6, and/or capable of hybridizing to the target sequence spanned by the primers amplifying the fragment from the housekeeping gene, such as the probe with the sequence of SEQ ID NO: 25 which is capable of hybridizing to the target sequence spanned by the primers with the sequence of SEQ ID NO: 10 and 11, respectively. If the specific PCR fragment is produced, the fluorescent-labeled probes are released at each PCR cycle and fluorescence signals can be detected. Comparison of the fluorescence signals detected for biological samples of interest with the fluorescence signals detected for appropriate control samples allows a semi-quantitative determination of the amount of GAT-OS3 DNA to the amount of total DNA in the biological sample.

Plants harboring GAT-OS3 are characterized by their glufosinate tolerance, which in the context of the present invention includes that plants are tolerant to the herbicide Liberty™. Tolerance to Liberty™ is defined by the criterion that spraying of the plants in the three to four leaf stage (3V to 4V) with at least 200 grams active ingredient/hectare (g.a.i./ha), preferably 500 g.a.i./ha, and possibly up to 1800 g.a.i./ha, does not kill the plants. Plants harboring GAT-OS3 can further be characterized by the presence in their cells of phosphinothricin acetyl transferase as determined by a PAT assay (De Block et al, 1987, supra).

Plants harboring GAT-OS3 are also characterized by having agronomical characteristics which, in the absence of weed pressure, are comparable to the following commercially available rice varieties in the US: Cocodrie, Priscilla, Cypress, Bengal, Cocodrie, Jefferson, Lemont, Drew, Kaybonnet, and Lagrue. The agronomical characteristics of relevance are: plant height, strength/stiffness of straw, resistance to lodging, leaf morphology (length, width, and angle for flag leaf), time to maturity, floret configuration, panicle fertility, complete closure of the hull on the seed, grain size and shape, and grain production and yield. The presence of a herbicide tolerance gene in the insertion region of the rice plant genome described herein confers, in the presence of weed pressure, superior agronomic characteristic to the plant of the invention when compared to similar commercially available rice varieties.

The following examples describe the identification of elite event GAT-OS3 and the development of tools for the specific identification of elite event GAT-OS3 in biological samples.

Unless otherwise stated, all recombinant DNA techniques are carried out according to standard protocols as described in Sambrook et al. (1989)*Molecular Cloning: A Laboratory Manual*, Second Edition, Cold Spring Harbour Laboratory Press, NY and in Volumes 1 and 2 of Ausubel et al. (1994) *Current Protocols in Molecular Biology*, Current Protocols, USA. Standard materials and methods for plant molecular work are described in Plant Molecular Biology Labfax (1993) by R. D. D. Croy published by BIOS Scientific Publications Ltd (UK) and Blackwell Scientific Publications, UK, and in "Brown T A, (1998) Molecular Biology LabFax, 2nd Edition, Academic Press, San Diego". Standard materials and methods for polymerase chain reactions (PCR) can be found in "McPherson MJ and Møller SG (2000) *PCR* (The Basics), BIOS Scientific Publishers Ltd., Oxford" and in "PCR Applications Manual," 3rd Edition (2006), Roche Diagnostics GmbH, Mannheim, which can be found at the Roche Applied Science website.

In the description and examples, reference is made to the following sequences:

SEQ ID NO: 1: nucleotide sequence comprising a 5' flanking region of GAT-OS3
SEQ ID NO: 2: nucleotide sequence comprising a 3' flanking region of GAT-OS3
SEQ ID NO: 3: primer OSA010
SEQ ID NO: 4: primer OSA009
SEQ ID NO: 5: primer SHA040
SEQ ID NO: 6: primer SHA041
SEQ ID NO: 7: primer YTP172
SEQ ID NO: 8: primer OSA001
SEQ ID NO: 9: primer OSA002
SEQ ID NO: 10: primer KVM159
SEQ ID NO: 11: primer KVM160
SEQ ID NO: 12: BamHI linker
SEQ ID NO: 13: BamHI linker
SEQ ID NO: 14: primer YTP110
SEQ ID NO: 15: primer YTP122
SEQ ID NO: 16: primer MLD015
SEQ ID NO: 17: primer MLD016
SEQ ID NO: 18: primer MDB010
SEQ ID NO: 19: primer MDB053
SEQ ID NO: 20: primer YTP160
SEQ ID NO: 21: primer YTP161
SEQ ID NO: 22: blunt-end GW adaptor
SEQ ID NO: 23: insertion site of GAT-OS3
SEQ ID NO: 24: GAT-OS3-specific oligonucleotide
SEQ ID NO: 25: phospholipase D gene-specific oligonucleotide

EXAMPLES

Example 1

Transformation of Rice

Rice tissue of the Cocodrie cultivar was transformed with a vector comprising the coding sequence of a modified bialaphos resistance gene (bar; Thompson et al., 1987, EMBO J. 6: 2519-2523) encoding the enzyme phosphinothricin acetyl transferase (PAT) under control of the 35S promoter from Cauliflower Mosaic Virus (Odell et al., 1985, Nature 313: 810-812) using Agrobacterium-mediated transformation. Selection was done on phosphinothricin (PPT) at all stages except plantlet regeneration, which was done in the absence of PPT to accelerate growth. This resulted in a total of 233 primary transformants (plants of generation $T_0$).

Example 2

Development of Events 2.1. Development of Transgenic Homozygous Lines

The various $T_0$ hemizygous plantlets were transitioned from tissue culture, transferred to greenhouse soil, and allowed to flower and set seed. Plantlets were evaluated for fertility, fecundity and tolerance to glufosinate ammonium. 185 events were selected for further analysis. T1 seed produced by selfing was collected from these plants.

T1 plants were grown in the field in Puerto Rico. T1 plants were sprayed with Liberty™ herbicide at 1800 grams active ingredient per hectare (g.a.i./ha; recommended dosage for farmers is 500 g.a.i./ha). Tolerant plants were evaluated for damage (which is defined by the criteria of leaf tip burn, mottling, stunting, yellowing or inability to recover from the herbicide application).

T2 seeds were harvested from panicles of 140, 504 and 54 tolerant plants of three selected events (named "1", "2" and "4" hereinafter). The populations were sown in rows at the LSU Rice Research Station in Crowley La. T2 plants were sprayed with Liberty™ herbicide (1800 g.a.i./ha) to evaluate segregation of the herbicide tolerance. 46, 133 and 16 populations were not susceptible to Liberty™ and thus considered to be homozygous for the bar gene insertion. The populations were selected as lines within events that survived the herbicide application. Tolerant populations versus susceptible populations demonstrated a segregation pattern of 2:1 for herbicide tolerance for two events (event "1" and "4"). In the T2 field evaluation, one of these events ("4") displayed shattering tendencies that were observed at maturity.

T3 seeds were collected from selected rows within the two event populations and were planted again to further evaluate herbicide tolerance in Puerto Rico. Further purification and selection of lines within the events was done based on uniformity (within and between rows). Seed from this increase was used for testing and evaluation.

T4 plots were grown in Louisiana and Mississippi. Seedling vigor, stand establishment, crop injury after spraying, heading, height, straw strength, disease, straight-head susceptibility and numerous phenotypic traits were noted.

2.2. Characterization of Transgenic Events—Selection of GAT-OS3

Transgenic events were further characterized for southern blot patterns, general phenotype and agronomic performance, and yield. Where appropriate these characteristics were determined in field conditions.

Southern Blot Analysis

Presence of the transgene was checked by standard Southern blot analysis using enzymatic digestion of rice genomic DNA with BamHI, which cuts after the bar gene, and hybridization to a restriction fragment of the transformation vector comprising the bar gene. The relative band intensity provided an indication on whether plants were homozygous or hemizygous for the transgenic locus. 20 out of 31 tested events were found to have simple insertions. This was confirmed by the fact that the segregation pattern of the transgene could be explained by Mendelian inheritance of a simple locus. The Chi square analysis for three populations of T2 panicle rows confirmed events "1" and "4" to be single locus events. For event "2", 2 rows of 15 did not meet the Chi square test for single locus.

General Plant Phenotype and Agronomic Performance

T1, T2 and T3 plants were evaluated for a number of phenotypic traits including plant height, strength/stiffness of straw, tendency to lodge, leaf morphology (too thin or incorrect angle for flag leaf), late maturity, floret configuration, panicle sterility or incomplete fertility, incomplete closure of the hull on the seed (which would lead to increased disease susceptibility), grain size and shape, and grain production and yield.

Lines were evaluated to be similar (or improved) in displayed agronomic characteristics compared to the untransformed Cocodrie cultivar and the following rice varieties: Priscilla, Bengal, Cypress, Jefferson, Lemont, Drew, Kaybonnet, Lagrue. No plants within a panicle row were kept which segregated for somaclonal variation for one or more of the above-mentioned traits.

Field Trials for Yield Evaluation

T4 lines from events "1" and "4" were tested for yield performance in different locations including Louisiana and Mississippi.

Statistical analysis of the agronomic parameters and ranking statistics of the plant morphology and other non-parametric data were completed to identify the best commercial candidate to compete with the parent variety Cocodrie and the following rice varieties: Priscilla, Cypress, Bengal, Jefferson, Lemont, Drew, Kaybonnet, and Lagrue.

GAT-OS3 was the event showing the most utility for producing a range of breeding lines.

Example 3

Characterization of Elite Event GAT-OS3

Once the GAT-OS3 event was identified as the event in which expression of the transgene as well as overall agronomic performance were optimal, the locus of the transgene was analyzed in detail on a molecular level.

3.1. Identification of the Flanking Regions of Elite Event GAT-OS3

3.1.1. 5' Flanking Region

The sequence of the region 5' flanking the foreign DNA in the GAT-OS3 elite event was determined using LIM TAIL-PCR. This protocol is a modification of the thermal asymmetric interlaced (TAL-) PCR method described by Liu et al. (1995, Plant J. 8(3): 457-463). Three nested primers, selected for annealing to the foreign DNA and based on their annealing conditions, were used in successive reactions together with primers annealing to linkers on BamHI restriction fragments of genomic DNA from rice plants containing elite event GAT-OS3. The tertiary PCR product was purified and sequenced.

The sequences of the linker and primers used were:

| Description | Primer | Sequence (5'→3') |
|---|---|---|
| BamHI linker | YTP108 | CTg.Agg.TCg.ACT.ATC.gAg.TT (SEQ ID NO: 12) |
| | YTP109 | gAT.CAA.CTC.gAT.AgT.CgA.CCT.Cag (SEQ ID NO: 13) |

-continued

| Description | Primer | Sequence (5'→3') |
|---|---|---|
| Linker primers | YTP110 | gTC.gAC.TAT.CgA.gTT (SEQ ID NO: 14) |
| | YTP122 | ACT.ATC.gAg.TTg.ATC (SEQ ID NO: 15) |
| Insert-specific primer (primary TAIL) | MLD015 | Tgg.TTC.CTA.gCg.TgA.gCC.AgT.g (SEQ ID NO: 16) |
| Insert-specific primer (secondary TAIL) | MLD016 | AgC.TgC.TgC.TCT.TgC.CTC.TgT (SEQ ID NO: 17) |
| Insert-specific primer (tertiary TAIL) | MLD017 = OSA009 | ggA.CCg.TTA.TAC.ACA.ACg.TAg (SEQ ID NO: 4) |

The fragment identified as comprising the 5' flanking region obtained by the LIM TAIL-PCR method was sequenced (SEQ ID NO: 1). The sequence between nucleotide 1 and 603 corresponds to plant DNA, while the sequence between nucleotide 604 and 743 corresponds to foreign DNA.

3.1.2. 3' Flanking Region

The sequence of the region 3' flanking the foreign DNA in the GAT-OS3 elite event was determined using a "Genome-Walker-PCR" (Clontech, Siebert P. D. et al. (1995) Nucl. Acids Res. 23:1087-1088). Primers annealing to adaptors on StuI restriction fragments of genomic DNA from rice plants containing elite event GAT-OS3 were used together with primers specific for the foreign DNA sequence.

The sequences of the adaptor and primers used were:

| Description | Primer | Sequence (5'→3') |
|---|---|---|
| Insert-specific primers | MDB010 | gCA.CCA.TCg.TCA.ACC.ACT.ACA.TCg (SEQ ID NO: 18) |
| | MDB053 | CAT.gAC.gTg.ggT.TTC.Tgg.CAg.C (SEQ ID NO: 19) |
| Adaptor primers | YTP160 | gTA.ATA.CgA.CTC.ACT.ATA.ggg.C (SEQ ID NO: 20) |
| | YTP161 | ACT.ATA.ggg.CAC.gCg.Tgg.T (SEQ ID NO: 21) |
| Blunt-end GW adaptor | YTP158 | gTA.ATA.CgA.CTC.ACT.ATA.ggg.CAC.gCg.Tgg.TCg.ACg.gCC.Cgg.gCT.ggT (SEQ ID NO: 22) |
| | YTP165 | ACCAgCCC-NH2 |

The fragment identified as comprising the 3' flanking region obtained by the Genome-Walker-PCR method was sequenced (SEQ ID NO: 2). The sequence between nucleotide 1 and 72 corresponds to foreign DNA, while the sequence between nucleotide 73 and 607 corresponds to plant DNA.

3.2. Identification of the Pre-Insertion Plant DNA

Using primers corresponding to sequences within the flanking regions of the foreign DNA on the wild-type *Oryza sativa* cv. Cocodrie as a template, the insertion site of the transgene was identified.

The following primers were used:

OSA010:
5'-CTA.CTA.gTA.CCC.gCT.gAC.TgC-3' (SEQ ID NO: 3)

(target: plant DNA of the 5' flanking region—sequence corresponds to the nucleotide sequence of SEQ ID NO: 1 from nucleotide 466 to nucleotide 486)

YTP172:
5'-AgT.AgT.ACT.TAC.CAg.CgA.Tgg-3' (SEQ ID NO: 7)

(target: plant DNA of the 3' flanking region—sequence corresponds to the complement of the nucleotide sequence of SEQ ID NO: 2 from nucleotide 131 to nucleotide 151)

This yielded a 234 bp fragment (SEQ ID NO: 23) in which nucleotide 139 to 157 corresponds to a target site deletion.

3.3. Genetic Analysis of the Locus

The genetic stability of the insert was checked by molecular and phenotypic analysis in the progeny plants over several generations.

Southern blot analyses on glufosinate resistant plants of GAT-OS3 rice plants of the T0, T1 and T2 generation were compared and were found to be identical. This proves that the molecular configuration of the transgene in GAT-OS3 containing plants was stable.

The GAT-OS3 event displayed Mendelian segregation for the transgene as a single genetic locus in at least three subsequent generations indicating that the insert is stable.

On the basis of the above results GAT-OS3 was identified as an elite event.

Example 4

Development of a Polymerase Chain Reaction Identification Protocol for Elite Event GAT-OS3

4.1. Primers

Specific primers were developed which recognize sequences within the elite event. More particularly, a primer was developed which recognizes a sequence within the 5' flanking region of GAT-OS3. A second primer was then selected within the sequence of the foreign DNA so that the primers span a sequence of about 278 nucleotides. The following primers were found to give particularly clear and reproducible results in a PCR reaction on GAT-OS3 DNA:

OSA010:
5'-CTA.CTA.gTA.CCC.gCT.gAC.TgC-3' (SEQ ID NO: 3)

(target: plant DNA—sequence corresponds to the nucleotide sequence of SEQ ID NO: 1 from nucleotide 466 to nucleotide 486)

OSA009:
5'-ggA.CCg.TTA.TAC.ACA.ACg.TAg-3' (SEQ ID NO: 4)

(target: insert DNA—sequence corresponds to the complement of the nucleotide sequence of SEQ ID NO: 1 from nucleotide 723 to nucleotide 743)

Primers targeting an endogenous sequence are preferably included in the PCR cocktail. These primers serve as an internal control in unknown samples and in the DNA positive control. A positive result with the endogenous primer pair demonstrates that there is ample DNA of adequate quality in the genomic DNA preparation for a PCR product to be generated. The endogenous primers were selected to recognize a housekeeping gene in rice:

```
OSA001:
5'-gAT.CAg.TgC.Agg.CAA.TAC.Tgg-3'    (SEQ ID NO: 8)
```

(Phospholipase D gene Acc. NO: AB001919, 3836→3856)

```
OSA002:
5'-TTC.CTA.ACA.TgT.ggg.TgT.Cg-3'    (SEQ ID NO: 9)
```

(Phospholipase D Gene Acc. No: Ab001919, 4291→4272)

4.2. Amplified Fragments

The expected amplified fragments in the PCR reaction are:
For primer pair OSA010-OSA009: 278 bp (GAT-OS3 elite event)
For primer pair OSA001-OSA002: 456 bp (endogenous control)

4.3. Template DNA

Template DNA was prepared from a leaf punch according to Edwards et al. (Nucleic Acid Research, 19, p 1349, 1991). When using DNA prepared with other methods, a test run utilizing different amounts of template should be done. Usually 50 ng of genomic template DNA yields the best results.

4.4. Assigned Positive and Negative Controls

To avoid false positives or negatives, it was determined that the following positive and negative controls should be included in a PCR run:

Master Mix control (DNA negative control). This is a PCR in which no DNA is added to the reaction. When the expected result, no PCR products, is observed this indicates that the PCR cocktail was not contaminated with target DNA.

A DNA positive control (genomic DNA sample known to contain the transgenic sequences). Successful amplification of this positive control demonstrates that the PCR was run under conditions which allow for the amplification of target sequences.

A wild-type DNA control. This is a PCR in which the template DNA provided is genomic DNA prepared from a non-transgenic plant. When the expected result, no amplification of a transgene PCR product but amplification of the endogenous PCR product, is observed this indicates that there is no detectable transgene background amplification in a genomic DNA sample.

4.5. PCR Conditions

Optimal results were obtained under the following conditions:
the PCR mix for 50 µl reactions contains:
5 µl template DNA
5 µl 10× Amplification Buffer (supplied with Taq polymerase)
1 µl 10 mM dNTP's
1 µl OSA001 (10 pmoles/µl)
1 µl OSA002 (10 pmoles/µl)
2 µl OSA009 (10 pmoles/µl)
2 µl OSA010 (10 pmoles/µl)
0.2 µl Taq DNA polymerase (5 units/µl)
water up to 50 µl the thermocycling profile to be followed for optimal results is the following:
4 min. at 95° C.
Followed by: 1 min. at 95° C.
1 min. at 57° C.
2 min. at 72° C.
For 5 cycles
Followed by: 30 sec. at 92° C.
30 sec. at 57° C.
1 min. at 72° C.
For 22 to 25 cycles
Followed by: 5 minutes at 72° C.

4.6. Agarose Gel Analysis

To optimally visualize the results of the PCR it was determined that between 10 and 20 µl of the PCR samples should be applied on a 1.5% agarose gel (Tris-borate buffer) with an appropriate molecular weight marker (e.g. 100 bp ladder AP-Biotech).

4.7. Validation of the Results

It was determined that data from transgenic plant DNA samples within a single PCR run and a single PCR cocktail should not be acceptable unless 1) the DNA positive control shows the expected PCR products (transgenic and endogenous fragments), 2) the DNA negative control is negative for PCR amplification (no fragments) and 3) the wild-type DNA control shows the expected result (endogenous fragment amplification).

When following the PCR identification protocol for GAT-OS3 as described above, lanes showing visible amounts of the transgenic and endogenous PCR products of the expected sizes, indicate that the corresponding plant from which the genomic template DNA was prepared, has inherited the GAT-OS3 elite event. Lanes not showing visible amounts of either of the transgenic PCR products and showing visible amounts of the endogenous PCR product, indicate that the corresponding plant from which the genomic template DNA was prepared, does not comprise the elite event. Lanes not showing visible amounts of the endogenous and transgenic PCR products, indicate that the quality and/or quantity of the genomic DNA did not allow for a PCR product to be generated. These plants cannot be scored. The genomic DNA preparation should be repeated and a new PCR run, with the appropriate controls, has to be performed.

4.8. Use of Discriminating PCR Protocol to Identify GAT-OS3

Before attempting to screen unknowns, a test run, with all appropriate controls, has to be performed. The developed protocol might require optimization for components that may differ between labs (template DNA preparation, Taq DNA polymerase, quality of the primers, dNTP's, thermocyler, etc.).

Amplification of the endogenous sequence plays a key role in the protocol. One has to attain PCR and thermocycling conditions that amplify equimolar quantities of both the endogenous and transgenic sequence in a known transgenic genomic DNA template. Whenever the targeted endogenous fragment is not amplified or whenever the targeted sequences are not amplified with the same ethidium bromide staining intensities, as judged by agarose gel electrophoresis, optimization of the PCR conditions may be required.

Rice leaf material from plants comprising different transgenic events was tested according to the above-described protocol. Samples from Cocodrie wild-type were taken as negative control.

Figure 2:
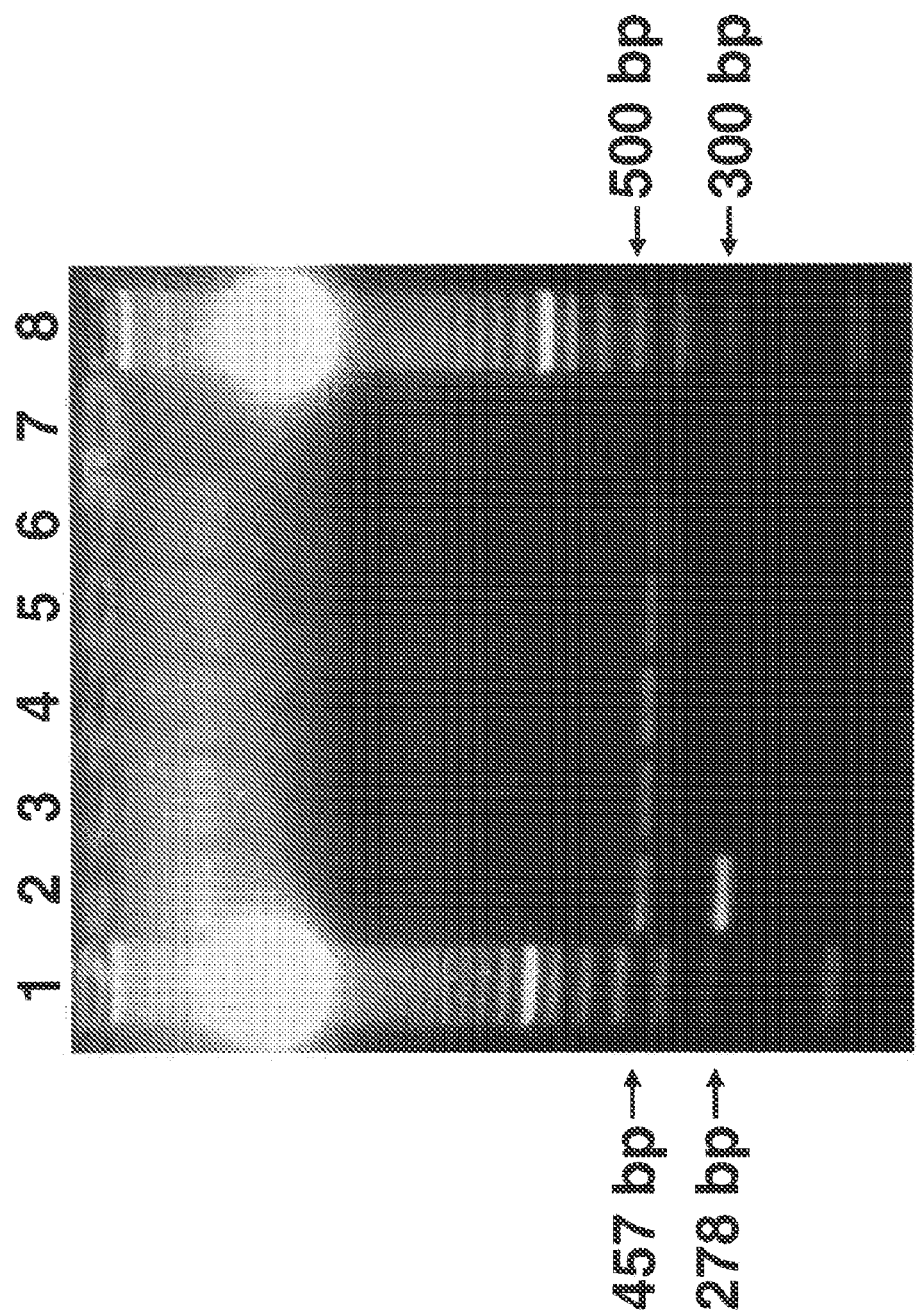
FIG. 2 represents results obtained by the PCR identification protocol developed for GAT-OS3. Loading sequence of the gel: Lane 1: molecular weight marker (100 bp ladder); lane 2: DNA samples from rice plant comprising the GAT-OS3 elite event; lanes 3 to 5: DNA samples from rice plants not comprising the GAT-OS3 elite event, but comprising different transgenic events; lane 6: control DNA sample from wild-type rice plant; lane 7: DNA negative control; lane 8: molecular weight marker (100 bp ladder).

FIG. 2 illustrates the result obtained with the elite event PCR identification protocol for GAT-OS3 on a number of rice plant samples. The sample in lane 2 was found to contain the elite event as the 278 bp band was detected, while the samples in lanes 3 to 5 did not comprise the GAT-OS3 elite event. Lane 6 represents a non-transgenic rice control; lane 7 represents the negative control (water) sample, and lanes 1 and 8 represent the Molecular Weight Marker (100 bp ladder).

Example 5

Use of a Specific Integration Fragment as a Probe for Detection of Material Comprising Elite Event GAT-OS3

A specific integration fragment of GAT-OS3 is obtained by PCR amplification using specific primers OSA010 (SEQ ID NO: 3) and OSA009 (SEQ ID NO: 4) or by chemical synthesis and is labeled. This integration fragment is used as a specific probe for the detection of GAT-OS3 in biological samples. Nucleic acid is extracted from the samples according to standard procedures. This nucleic acid is then contacted with the specific probe under hybridization conditions which are optimized to allow formation of a hybrid. The formation of the hybrid is then detected to indicate the presence of GAT-OS3 nucleic acid in the sample. Optionally, the nucleic acid in the samples is amplified using the specific primers prior to contact with the specific probe. Alternatively, the nucleic acid is labeled prior to contact with the specific probe instead of the integration fragment. Optionally, the specific probe is attached to a solid carrier (such as, but not limited to a filter, strip or beads), prior to contact with the samples.

Example 6

Protocol for the Real-Time PCR-Based Detection of GAT-OS3 DNA and Relative Quantification of GAT-OS3 DNA to Total DNA in Rice Plant Material For specific detection of GAT-OS3 event genomic DNA, a fragment of 66 bp spanning the insert-to-plant junction in GAT-OS3 is amplified using two specific primers. PCR products are measured during each cycle (real-time) by means of a GAT-OS3-specific oligonucleotide probe labeled with fluorescent dyes.

For relative quantification of GAT-OS3 event genomic DNA, a rice-specific Reference system is used which amplifies a 68-bp fragment of a rice endogenous gene, phospholipase D, using a pair of phospholipase D-specific primers and a phospholipase D-specific probe labeled with fluorescent dyes.

6.1. Primers and Probes
6.1.1. Primers and Probes for Detection of GAT-OS3 DNA ("Target System"):

Specific primers were developed which recognize sequences within the elite event. More particularly, a primer was developed which recognizes a sequence within the 3' flanking region of GAT-OS3. A second primer was then selected within the sequence of the foreign DNA so that the primers span a sequence of about 66 nucleotides. The following primers were found to give particularly clear and reproducible results in a real time PCR reaction on GAT-OS3 DNA:

SHA040:
5'-TCT.Agg.ATC.CgA.AgC.AgA.TCg.T-3'  (SEQ ID NO: 5)

(target: insert DNA—sequence corresponds to the nucleotide sequence of SEQ ID NO: 2 from nucleotide 49 to nucleotide 70)

SHA041:  5'-ggA.ggg.CgC.ggA.gTg.T-3'  (SEQ ID NO: 6)

(target: plant DNA—sequence corresponds to the complement of the nucleotide sequence of SEQ ID NO: 2 from nucleotide 99 to nucleotide 114)

A GAT-OS3-specific oligonucleotide probe was developed which recognizes a sequence within the sequence spanned by primers SHA040 and SHA041 and labeled with FAM as a reporter dye at its 5' end and TAMRA as a quencher at its 3' end:

(SEQ ID NO: 24)
TM098:   5'-CCA.CCT.CCC.AAC.AAT.AAA.AgC.gCC.Tg-3'

(target: insert/plant junction DNA—sequence corresponds to the nucleotide sequence of SEQ ID NO: 2 from nucleotide 72 to nucleotide 97)

6.1.2. Primers and Probes for Relative Quantification of GAT-OS3 DNA ("Reference System"):

Primers were developed targeting an endogenous gene, the phospholipase D gene sequence. More particularly, two primers were developed each recognizing a sequence within the phospholipase D gene sequence and directed towards each other so that the primers span a sequence of about 68 nucleotides. The following primers were found to give particularly clear and reproducible results:

KVM159:
5'-Tgg.TgA.gCg.TTT.TgC.AgT.CT-3'  (SEQ ID NO: 10)

(Phospholipase D gene Acc. NO: AB001919, 3774→3793)

(SEQ ID NO: 11)
KVM160:   5'-CTg.ATC.CAC.Tag.CAg.gAg.gTC.C-3'

(Phospholipase D Gene Acc. No: Ab001919, 3841→3820)

A phospholipase D-specific probe was developed which recognizes a sequence within the sequence spanned by primers KVM159 and KVM160 and labeled with VIC as a reporter dye at its 5' end and TAMRA as a quencher at its 3' end:

(SEQ ID NO: 25)
TM013:   5'- TgT.TgT.gCT.gCC.AAT.gTg.gCC.Tg -3'

(Phospholipase D Gene Acc. No: Ab001919, 3795→3817)
6.2. Measured Fluorescence Signals The PCR protocol has been optimized for use in an ABI Prism® 7500 sequence detection system (uses fluorescent-based PCR chemistries to provide quantitative detection of nucleic acid sequences using real-time analysis and qualitative detection of nucleic acid sequences using end-point and association-curve analysis). Other systems may be used, but thermal cycling conditions must be verified.

It was determined that separate amplification curves for each primer/probe system (Target and Reference system) are preferably generated in the same analytical amplification run.

The measured fluorescence signal passes a threshold value after a certain number of cycles. This threshold cycle is called the "Ct" value. For quantification of the amount of GAT-OS3 DNA in a test sample, Reference and Target Ct values are determined and subtracted, generating the ΔCt value for the sample. The ΔCt value of a positive control sample is then subtracted from the ΔCt value of the test sample to produce the ΔΔCt value of the test sample, which is used to determine the level of the GAT-OS3 event in the test DNA sample.

6.3. Test Samples

The protocol was optimized for analysis of 100 ng DNA extracted from seed or grain bulk samples (3,000 seeds/grain) containing mixtures of rice harboring the GAT-OS3 sequence and conventional rice.

It was determined that for each sample (e.g., a seed or grain lot) under examination, 2 representative test samples of 40 grams should be taken. On each test sample one DNA extraction should be performed followed by two replicate Real time PCR reactions.

6.4. Control Samples

To avoid false positives and negatives, it was determined that the following control samples should be included for each PCR:

"Positive Seed Control" bulk sample (PSC): 100 ng of DNA extracted from a 3,000 seed bulk sample containing 1 homozygous GAT-OS3 event-containing seed "Negative Seed Control" bulk sample (NSC): 100 ng of DNA extracted from conventional rice seeds "Limit Of Detection" control bulk sample ("LOD"): 100 ng of DNA extracted from a 6,000 seed bulk sample containing 1 homozygous GAT-OS3 event-containing seed No Template Control sample (NTC): A sample of the PCR matrix containing no template DNA.

For the analysis of PSC and NSC control samples, DNA extractions are performed in duplicate on one powder sample, followed by duplicate Real-time PCR reactions per DNA extract.

For the analysis of the "LOD" control sample one DNA extraction is performed per seed/grain lot analyzed, followed by duplicate Real-time PCR reactions per DNA extract.

6.5. PCR Conditions

Optimal results were obtained under the following conditions:

PCR mix for Target System:
the PCR mix for 25 μl reactions contains:
5 μl template DNA (100 ng)
12.5 μl 2× TaqMan® Universal PCR Master Mix
1 μl SHA040 (10 μM)
1 μl SHA041 (10 μM)
0.5 μl TM098 (10 μM)
5 μl water PCR mix for Reference System:
the PCR mix for 25 μl reactions contains:
5 μl template DNA (100 ng)
12.5 μl 2× TaqMan® Universal PCR Master Mix
0.5 μl KVM159 (10 μM)
0.5 μl KVM160 (10 μM)
0.5 μl TM013 (10 μM)
6 μl water Thermocycling Profile:
2 min. at 50° C.
10 min. at 95° C.
Followed by: 15 sec. at 95° C.
1 min. at 60° C.
For 45 cycles

6.6. Data Analysis and Calculations

Data Analysis:

Subsequent to the real-time PCR, the run is analyzed following the procedure below:

1. From cycles 3 to 15 the default baseline range is used.
2. The threshold is set by displaying the amplification curves of one system (e.g. Target system) using the ΔRn-axe displayed in the logarithmic mode, locating the threshold line in the centre of the area where the amplification profiles are parallel (exponential phase of PCR) and where there is no "fork effect" between repetitions of the same sample, and by pressing the update button to ensure changes affect the Ct values.
3. The procedure described under 1) and 2) is repeated on the amplification plots of the other system (e.g. Reference system).

After having defined a threshold value within the logarithmic phase of amplification as described above, the instrument's software calculates the Ct-values for each reaction.

Calculations:

Following calculations are performed to determine the relative amount of GAT-OS3 DNA in a sample:

1. ΔCt values are calculated for all Test and Control samples by subtracting the endogenous reference specific Ct value from the target specific Ct value.

$$\Delta Ct = Ct_{target} - Ct_{endo}$$

2. ΔΔCt values are calculated for all Test samples by subtracting their ΔCt values from the averaged ΔCt value of the Positive Seed Control bulk samples (PSC).

$$\Delta\Delta Ct = \Delta Ct_{test\,sample} - \Delta Ct_{PSC}$$

3. The ΔΔCt values of all Test samples are compared to the ΔΔCt acceptance requirement limit. This limit has been determined to be 4.

6.7. Validation of the Results

Acceptance Criteria

It was determined that semi-quantitative real-time PCR data from a Test sample should not be acceptable unless the following conditions are met:

For the PSC sample: Reference Ct value is below 24 and Target Ct value is 9-13 higher than the endogenous Ct value.

For the NSC sample: Reference Ct value is below 24 and ΔΔCt value is above the ΔΔCt acceptance requirement limit, determined to be 4 (This ΔΔCt value determines the background signal and is experimentally determined as a safe cut-off enabling one to minimize false negative and false positive scorings. It means that the normalized Target Ct value (ΔCt) for the sample has to be at least 4 cycles higher than the positive control sample, in order to be scored negative).

For the "LOD" sample: Reference Ct value is below 24 and ΔΔCt value is below the ΔΔCt acceptance requirement limit, determined to be 4 (see above).

For the NTC sample: Both Reference and Target Ct values show no significant amplification signals For the Test samples: Reference Ct value is below 24.

Results

A Test sample is scored positive for the Target if: Both calculated ΔΔCt values of one or both Test samples of an analyzed seedlot are below the ΔΔCt acceptance requirement limit.

A Test sample is scored negative for the Target if: All 4 calculated ΔΔCt values of both test samples of an analyzed seedlot are above the ΔΔCt acceptance requirement limit.

A Test sample is ambiguously scored if: One of the calculated ΔΔCt values of one or both of the test samples of an analyzed seedlot are below the ΔΔCt acceptance requirement limit.

The Real-time PCR analysis must be repeated on the inconclusive DNA Test sample(s) to obtain conclusive results:

If the ΔΔCt values of the test sample are conclusive (all below or above the ΔΔCt acceptance requirement limit) the scoring can be done as described above.

If again, one of the ΔΔCt values of the test sample are inconclusive, the level of GAT-OS3 DNA is below the detection limit of the method, thus the final score is "Negative".

Example 7

Protocol for the PCR-Based Determination of the Zygosity Status of GAT-OS3 Rice Plant Material 7.1. Primers Two primers recognizing the nucleotide sequences of the wild-type locus prior to insertion of the elite event are designed in such a way that they are directed towards each other and have the insertion site in between. This set of primers, together with a third primer complementary to foreign DNA sequences and directed towards the flanking DNA, allow simultaneous PCR amplification of the GAT-OS3 locus as well as of the wild-type locus.

7.2. Amplified Fragments

The sizes of the expected amplified fragments in the PCR reaction are determined based on the sequence of the 5' or 3' flanking regions and the foreign DNA continuous therewith (Example 3.1.) for the amplicon of the GAT-OS3 locus and the sequence of the insertion region (Example 3.2.) for the amplicon of the wild-type locus.

7.3. Template DNA

Template DNA is prepared from a leaf punch according to Edwards et al. (Nucleic Acid Research, 19, p 1349, 1991). Usually 50 ng of genomic template DNA yields the best results.

7.4. Assigned Positive and Negative Controls

To avoid false positives or negatives, it is advisable that the positive and negative controls as described in Example 4.4. are included in a PCR run.

7.5. PCR Conditions

PCR conditions analogous to those described in Example 4.5. are determined by optimizing all the components of the PCR reaction (template and primer concentrations, annealing and elongation temperatures, number of cycles, etc) until the results of the PCR, as visualized on an agarose gel, are in accordance with the conditions described in point 7.6. below.

7.6. Validation Results

Data from transgenic plant DNA samples within a single PCR run and a single PCR Master Mix will not be acceptable unless:

the positive control shows the expected PCR products (transgenic target amplification),
the wild-type-positive DNA control shows the expected result (wild-type target amplification),
the negative control is negative for PCR amplification (no fragments).

7.7. Use of the Zygosity Scoring Protocol for Identification of the Zygosity Status in GAT-OS3 Containing Plants Lanes showing visible amounts of the transgenic PCR product of the expected size and not showing visible amounts of the wild type PCR product, indicate that the corresponding plant from which the genomic DNA template was prepared, is homozygous for the transgenic gene cassette.

Lanes showing visible amounts of the transgenic and wild type PCR products of the expected sizes, indicate that the corresponding plant from which the genomic template DNA was prepared, is hemizygous for the transgenic gene cassette.

Lanes not showing visible amounts of the transgenic PCR product and showing visible amounts of the wild type PCR product, indicate that the corresponding plant from which the genomic template DNA was prepared, has not inherited the transgenic sequence assayed for and is thus homozygous for the wild type locus.

Lanes not showing visible amounts of transgenic and wild type PCR products, indicate that the quality and/or quantity of the genomic DNA did not allow for a PCR product to be generated. These plants cannot be scored. The genomic DNA preparation should be repeated and a new PCR run, with the appropriate controls, has to be performed.

Example 8

Introgression of GAT-OS3 into Preferred Cultivars

Elite event GAT-OS3 is introduced by repeated backcrossing into the following cultivars:

California Temperate Japonicas (such as but not limited to M204, M202, M201, M103)
California Tropical Japonicas (such as but not limited to L201, L202)
Japanese and Korean Temperate Japonicas (such as but not limited to Koshihikari and Milyang)
Australian Temperate Japonicas (such as but not limited to Kyeema)
Mediterranean Temperate Japonicas (such as but not limited to Ballila, Drago)
Chinese Indicas (such as but not limited to Guichao, Congui 314, Teqing)
Southern United State Tropical Japonicas, long grain (such as but not limited to Drew, Cypress, Jefferson)
Southern United State Tropical Japonicas, medium grain (such as but not limited to Bengal, Mars, Brazos, Mercury)
South American Tropical Japonicas, long grain (such as but not limited to El Paso 144, IRGA 409)
Far Eastern basmati and jasmine types (Kasmir, Kwao Dak Mali)
African javanica types (bulu rices)

It is observed that the introgression of the elite event into these cultivars does not significantly influence any of the desirable phenotypic or agronomic characteristics of these cultivars (no linkage drag) while expression of the transgene, as determined by glufosinate tolerance, meets commercially acceptable levels. This confirms the status of event GAT-OS3 as an elite event.

As used in the claims below, unless otherwise clearly indicated, the term "plant" is intended to encompass plant tissues, at any stage of maturity, as well as any cells, tissues, or organs taken from or derived from any such plant, including without limitation, any seeds, leaves, stems, flowers, roots, single cells, gametes, cell cultures, tissue cultures or protoplasts.

Reference seed comprising elite event GAT-OS3 was deposited as GAT-OS3 at the ATCC (10801 University Blvd., Manassas, Va. 20110-2209) on Oct. 16, 2000, under ATCC accession number GAT-2600.

The above description of the invention is intended to be illustrative and not limiting. Various changes or modifications in the embodiments described may occur to those skilled in the art. These can be made without departing from the spirit or scope of the invention.

All references cited herein (e.g., patents, publications, etc.) are herein incorporated by reference in entirety.

The invention claimed is:

1. A transgenic rice plant, or seed, cells, parts or progeny thereof, each comprising elite event GAT-OS3 in its genome, reference seed comprising said event having being deposited at the ATCC under accession number PTA-2600.

2. The transgenic rice plant, seed, cells, parts or progeny of claim 1, the genomic DNA of which, when analyzed using the PCR identification protocol for GAT-OS3 with two primers comprising the nucleotide sequence of SEQ ID NO: 3 and SEQ ID NO: 4 respectively, yields a DNA fragment of about 278 bp.

3. A seed comprising elite event GAT-OS3 deposited at the ATCC under accession number PTA-2600 or derivatives therefrom comprising elite event GAT-OS3.

4. A rice plant or a part thereof, or seed therefrom obtained from the seed of claim 3.

5. A rice plant, or seed, cells or tissues thereof, each comprising elite event GAT-OS3 in its genome, obtained by propagation of and/or breeding with a rice plant grown from the seed deposited at the ATCC under accession number PTA-2600.

6. A rice seed comprising elite event GAT-OS3, reference seed comprising said event having been deposited at the ATCC under accession number PTA-2600.

7. A transgenic rice plant, cell or tissue, comprising elite event GAT-OS3, produced from the seed of claim 6.

8. A method for producing a rice plant or seed comprising elite event GAT-OS3 comprising crossing a plant according to any one of claims 1 to 7 with another rice plant, and planting the seed obtained from said cross.

9. Rice genomic DNA comprising elite event GAT-OS3.

10. Genomic DNA comprising elite event GAT-OS3 produced from a rice plant, plant cell or seed according to any one of claims 1 to 7.

* * * * *